(12) United States Patent
Sathe et al.

(10) Patent No.: US 9,029,507 B2
(45) Date of Patent: May 12, 2015

(54) COPOLYMER-1, PROCESS FOR PREPARATION AND ANALYTICAL METHODS THEREOF

(75) Inventors: Dhananjay Govind Sathe, Mumbai (IN); Avinash Venkatraman Naidu, Mumbai (IN); Subramanian Sundaram, Mumbai (IN); Anindya Sibnath Bhattacharyya, Mumbai (IN); Rakesh Shekhawat, Mumbai (IN); Divya Lal Saksena, Mumbai (IN); Sukumar Ramanujam, Mumbai (IN); Sanjay Vyankatrao Patil, Mumbai (IN)

(73) Assignee: USV Limited (IN)

( * ) Notice: Subject to any disclaimer, the term of this patent is extended or adjusted under 35 U.S.C. 154(b) by 0 days.

(21) Appl. No.: 13/985,416

(22) PCT Filed: Feb. 14, 2012

(86) PCT No.: PCT/IN2012/000104
§ 371 (c)(1),
(2), (4) Date: Aug. 14, 2013

(87) PCT Pub. No.: WO2012/123959
PCT Pub. Date: Sep. 20, 2012

(65) Prior Publication Data
US 2013/0323771 A1  Dec. 5, 2013

(51) Int. Cl.
| | | |
|---|---|---|
| *C07K 1/00* | (2006.01) | |
| *C12Q 1/37* | (2006.01) | |
| *C07K 2/00* | (2006.01) | |
| *C07K 14/00* | (2006.01) | |
| *C08G 69/10* | (2006.01) | |
| *G01N 30/02* | (2006.01) | |
| *A61K 38/00* | (2006.01) | |

(52) U.S. Cl.
CPC . *C12Q 1/37* (2013.01); *A61K 38/00* (2013.01); *C07K 2/00* (2013.01); *C07K 14/001* (2013.01); *C08G 69/10* (2013.01); *G01N 30/02* (2013.01)

(58) Field of Classification Search
USPC .......................................................... 530/333
See application file for complete search history.

(56) References Cited

U.S. PATENT DOCUMENTS

| 2002/0115103 A1 | 8/2002 | Gad et al. |
|---|---|---|
| 2007/0059798 A1 | 3/2007 | Gad et al. |

FOREIGN PATENT DOCUMENTS

| WO | WO-2012016042 A2 | 2/2012 |
|---|---|---|
| WO | WO-2012016042 A3 | 2/2012 |
| WO | WO-2012123959 A2 | 9/2012 |

OTHER PUBLICATIONS

"International Application Serial No. PCT/IN2012/000104, International Search Report mailed Jan. 11, 2013", 7 pgs.
"International Application Serial No. PCT/IN2012/000104, International Written Opinion mailed Jan. 11, 2013", 9 pgs.

*Primary Examiner* — Bin Shen
(74) *Attorney, Agent, or Firm* — Schwegman Lundberg & Woessner, P.A.

(57) ABSTRACT

The present invention relates to analytical methods such as molecular weight determination of polypeptide, in particular Glatiramer acetate. The present invention further relates to an improved process for preparation of polypeptides or pharmaceutically acceptable salts thereof, particularly Glatiramer acetate also known as Copolymer-1. The present invention further relates to characterization of Glatiramer acetate by peptide mapping.

18 Claims, 9 Drawing Sheets

COPOLYMER-1, PROCESS FOR PREPARATION AND ANALYTICAL METHODS THEREOF

RELATED APPLICATION

This application is a U.S. National Stage Application filed under 35 U.S.C §371 of International Application Serial No. PCT/IN2012/000104, filed on 14 Feb. 2012, and published on 20 Sep. 2012 as WO 2012/123959 A2, which application claims benefits of Indian Provisional Application No. 409/MUM/2011, filed on 14 Feb. 2011, all of which applications and publication are incorporated herein by reference in their entireties.

FIELD OF THE INVENTION

The present invention relates to analytical methods such as molecular weight determination of polypeptide, in particular Glatiramer acetate. The present invention further relates to an improved process for preparation of polypeptides or pharmaceutically acceptable salts thereof, particularly Glatiramer acetate also known as Copolymer-1. The present invention further relates to characterization of Glatiramer acetate by peptide mapping.

BACKGROUND OF THE INVENTION

One of the more common neurologic diseases in human adults is multiple sclerosis. This condition is a chronic, inflammatory CNS disease characterized pathologically by demyelination in the brain and spinal cord. Glatiramer acetate (GA), also known as Copolymer-1, has been shown to be effective in treating multiple sclerosis (MS). Daily subcutaneous injections of Glatiramer acetate (20 mg/injection) reduces lesions, relapse rates and progression of disability (Johnson K. P. et al., Neurol., 1995, 45(7): 1268-76). Glatiramer acetate reduces the proportion of new MS lesions evolving into "black holes" (Filippi M. et al., Neurol., 2001, 57:731-733).

Glatiramer acetate (Copolymer-1) is marketed under the brand name COPAXONE®. It is approved for reducing the frequency of relapses in patients with Relapsing-Remitting Multiple Sclerosis (RRMS). Glatiramer acetate consists of the acetate salts of synthetic polypeptides, containing four naturally occurring amino acids: L-glutamic acid, L-alanine, L-tyrosine and L-lysine with an average molar fraction of 0.141, 0.427, 0.095 and 0.338 respectively. It is synthesized by chemically polymerizing the four amino acids to yield the product with the desired molecular weight range. The average molecular weight of Glatiramer acetate is 4,700-11,000 daltons [US label for lyophilized powder] or 5,000-9,000 daltons [US label for pre-filled syringe/Summary of Product Characteristics]. Copaxone comprises a mixture of polypeptides having different molecular weights and sequences.

The structural formula of Copaxone is

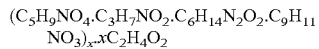

The process for preparation of Glatiramer acetate is described in Euro. J. Immun. 1, 242-248 (1971) [Tietelbaum et al] and U.S. Pat. No. 3,849,550 [Tietelbaum et al]. U.S. Pat. No. 3,849,550 discloses a process, wherein the N-carboxyanhydrides of tyrosine, alanine, γ-benzyl glutamate and ε-N-trifluoroacetyl lysine are polymerized at ambient temperature in anhydrous dioxane with diethylamine as initiator. The deblocking of the γ-carboxyl group of the glutamic acid is effected by hydrogen bromide in glacial acetic acid which is followed by the removal of the trifluoroacetyl groups from the lysine residues by 1M piperidine.

Process for preparation of copolymer-1 is also disclosed in U.S. Pat. No. 5,800,808, IN190759, U.S. Pat. No. 5,981,589, U.S. Pat. No. 6,054,430, U.S. Pat. No. 6,342,476, U.S. Pat. No. 6,362,161 and WO00/05250. These documents elaborate on the process for preparing copolymer-1 involving polymerization of four N-carboxyanhydrides of amino acids to obtain protected copolymer and deprotection of the protected copolymer using hydrogen bromide in acetic acid and piperidine to obtain deprotected copolymer which is then subjected to dialysis for purification and salt exchange.

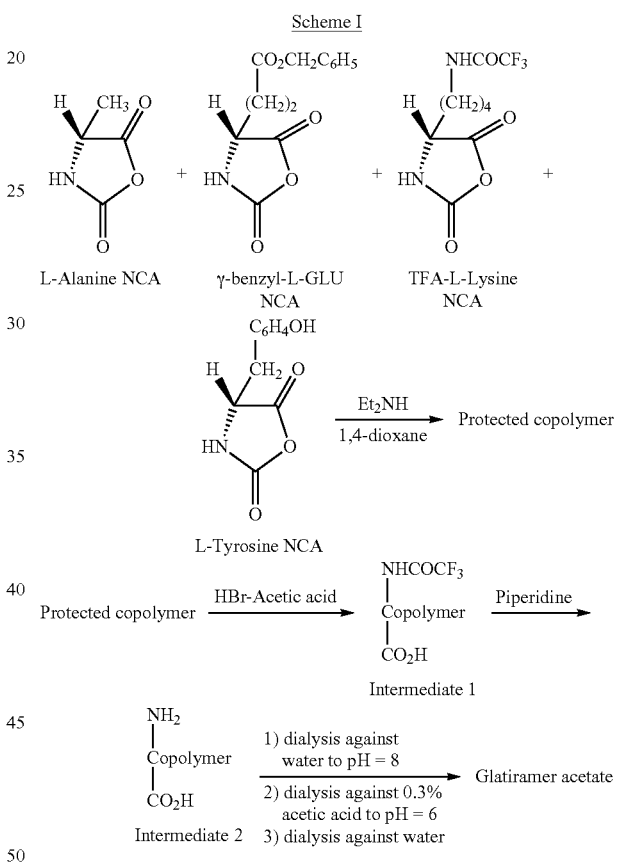

Scheme I

US20060172942 discloses process for preparation of Glatiramer acetate which involves polymerizing N-carboxyanhydrides of tyrosine, alanine, γ-benzyl glutamate and trifluoroacetyl lysine to obtain protected polypeptides. The benzyl protecting group from the protected polypeptides is removed by catalytic hydrogenolysis followed by removal of the trifluoroacetyl protecting group by contacting the polypeptide with an organic base. The free trifluoroacetyl groups and low molecular weight impurities are removed from the polypeptide mixture by ultrafiltration followed by contacting the polypeptide mixture with an aqueous solution of acetic acid to obtain the acetate salt of polypeptide.

U.S. Pat. No. 7,049,399 describes a process for the preparation of a polypeptide comprising polymerization of a mixture of the N-carboxyanhydrides of L-alanine, L-tyrosine, a protected L-glutamate and a protected L-lysine to obtain protected copolymer or salt thereof; deprotection of the protected copolymer (or salt thereof) to produce polypeptide or a pharmaceutically acceptable salt thereof in one single step; separation and purification of the polypeptide (or a pharmaceutically acceptable salt) to obtain a purified polypeptide. The deprotection of the protected copolymer is carried out either by catalytic transfer hydrogenation or catalytic hydrogenation under hydrogen pressure ranging from 40-100 psi and at temperature ranging from 50°-80° C.

The disadvantage with respect to the process disclosed in these documents is that hydrogenolysis requires high pressure and temperature, which in turn needs additional operation precaution on large scale, thus increasing the production cost. Since Copaxone is stable at a low temperature of 2° C. to 8° C., high temperature during final step may result in degradation of the product thereby reducing the quality and yield of the desired product.

WO2006050122 describes a two step process for preparing Glatiramer acetate. The process involves polymerizing a mixture of N-carboxyanhydride of L-tyrosine, N-carboxyanhydride of L-alanine, N-carboxyanhydride of protected L-glutamate and N-carboxyanhydride of N-protected L-lysine, in a polar aprotic solvent in presence of an initiator to form a protected Glatiramer; adding an acid and/or organic or inorganic base to the formed protected Glatiramer to form Glatiramer; and treating the obtained Glatiramer with acetic acid to form Glatiramer acetate. The deprotection of the protected Glatiramer is carried out by two different methods. First method for deprotection is by treatment with an acid and second method for deprotection is accomplished by treatment with alkaline earth metal hydroxide. The disadvantage of this process is that use of alkaline earth metal hydroxide for deprotection of peptides result in slow reactions and formation of high levels of the diastereomer resulting from racemization/epimerization of the stereogenic centers (Ahmed F. Abdel-Magid et. al., Tetrahedron Letters 39, 3391 (1998)).

WO2006029393 discloses a process of producing a mixture of trifluoroacetyl polypeptides which do not all have the same amino acid sequence, where each polypeptide consists essentially of alanine, glutamic acid, tyrosine and lysine, wherein the mixture has a desired average molecular weight comprising deprotecting a mixture of polypeptides each consisting essentially of alanine, γ-benzyl glutamate, tyrosine and trifluoroacetyl lysine with a solution of hydrobromic acid in acetic acid, which solution comprises less than 0.5% of free bromine and less than 1000 ppm of metal ion impurities. It further discloses that solution of hydrobromic acid in acetic acid having less than 0.5% of free bromine can be achieved by pretreating the solution with a bromine scavenger, preferably phenol to decrease the level of free bromine. It also discloses the use of 10% to 36% of hydrobromic acid in acetic acid.

US20080021200 discloses a process for preparing a polypeptide comprising L-tyrosine, L-alanine, L-glutamate and L-lysine, or a pharmaceutically acceptable salt thereof, wherein said process comprises, (a) polymerizing a mixture of N-carboxyanhydride of L-tyrosine, N-carboxyanhydride of L-alanine, N-carboxyanhydride of a protected L-glutamate and N-carboxyanhydride of a protected L-lysine, in a polar aprotic solvent in the presence of an initiator, to form a protected polypeptide; (b) admixing an acid with the protected polypeptide formed in Step (a) and a solvent, to form a product; and (c) admixing a substance selected from the group consisting of diisopropylamine, isopropylamine, ammonia, and mixtures thereof, with the product formed in Step (b), and water or a mixture of a solvent and water, to form a deprotected polypeptide or a pharmaceutically acceptable salt thereof. It further discloses that diisopropylamine and isopropylamine were the only amines that successfully removed the $N^\epsilon$-trifluoroacetyl group of lysine moiety. It also discloses that when diisopropylamine or isopropylamine is used for removal of trifluoroacetyl groups, a clear solution is obtained after about 1 hr or after about 1.5 hrs respectively.

WO2009016643 describes a process for preparation of Glatiramer acetate (Copolymer-1) where the trifluoroacetyl copolymer-1, obtained after the debenzylation reaction, is washed with an organic solvent to remove reactive benzyl bromide, generated as a reaction by-product. The released benzyl bromide is a highly reactive electrophile and reacts with nucleophiles like primary and secondary amines to generate unwanted N-alkylated products. Also it is highly lachrymatory and handling it in large quantities on commercial scale is hazardous and unsafe. WO'643 also discloses debenzylation reaction of protected copolymer-1 for shorter duration of time at a higher temperature and a method to remove benzyl bromide from the reaction mixture. Removal of benzyl protecting group of glutamic acid is affected by 33% hydrogen bromide in acetic acid at 35-45° C. for 1-5 hours thereby reducing the reaction time, and in order to eliminate benzyl bromide the filtered product is washed with an organic solvent. This method employs an additional organic solvent which is undesirable on a commercial scale. Thus the processes for preparation of Glatiramer acetate as disclosed above are industrially not feasible.

The inventors of the present invention have developed a simple, cost effective, efficient, commercially viable and consistent process for preparation of copolymer-1 (Glatiramer acetate). Use of 33% HBr leads to cleavage of the peptide bonds in the polymer resulting in low molecular weight compounds. The present invention provides a more commercially viable process for preparation of Glatiramer acetate by using about 7% to 20% HBr, preferably about 15% HBr in acetic acid for removal of the benzyl protecting group at room temperature, preferably at about 23° C. to 30° C., more preferably at about 25° C., most preferably at 25° C.±0.2° C. The present invention further provides a process for preparation of Glatiramer acetate where the wet solid obtained after the first deprotection step is not subjected to drying and is used as such for the further reaction which saves considerable time and hence is considered to be an industrially viable process. The present invention further provides a process for removal of the trifluoroacetyl protecting group using amine, preferably secondary amine such as dialkyl amine selected from diethylamine, dimethyl amine or diisopropylamine, preferably diethyl amine.

Prior art provides methods for determination of molecular weight of Polypeptides, in particular Glatiramer acetate. WO200018794 (WO'794) discloses use of a plurality of molecular weight markers to establish a relationship between retention time on a chromatographic column and molecular weight for determination of average molecular weight of glatiramer acetate batches. Each of these molecular weight markers disclosed in WO'794 is a polypeptide and has a pre-determined amino acid sequence and defined molecular weight. The present invention provides the use of polypeptide fractions (molecular weight markers), obtained by subjecting Copaxone/Glatiramer acetate/Glatiramoids to Size Exclusion Chromatography (SEC) or Gel Permeation Chromatography (GPC), for determination of molecular weight of Glatiramer acetate batches. The polypeptide fractions (molecular weight markers) obtained by the process of the present invention has a defined molecular weight. However, the amino acid sequence of these polypeptide fractions are random.

Another analytical technique used for characterizing a polypeptide/protein is Peptide Mapping. Peptide mapping is a comparative procedure where the information obtained, compared to a reference standard or reference material similarly treated, confirms the primary structure of the polypeptide/protein. This helps in detecting whether alterations in structure have occurred and demonstrates process consistency and genetic stability. WO2010129851 provides a process whereby hydrolysis enzymes are used to digest a standard of a complex mixture of polypeptides such as Glatiramer acetate, into several peptide fragments. The peptide fragments are analyzed by mass spectrometry. The mass spectrometric results of each sample are used as the fingerprint for comparison with other samples. Each peptide fragment detected by the first mass analyzer is selected and subjected to second mass spectometric analysis to cleave the precursor peptide ions into even smaller fragments. The mass spectra obtained from MS/MS analysis are analyzed by the software such as Biotools to obtain the sequence of each peptide fragment.

Expert Opin. Pharmacother. (2009) 10(4) discloses that polypeptide mapping using capillary electrophoresis separation of polypeptide fragments obtained after digestion with trypsin and mapping based on proteolytic hydrolysis by carboxypeptidase P followed by separation of the fragments by reverse-phase HPLC are methods of discerning sequence differences among GA structures and those of other glatiramoids. Carboxypeptidase P is an expensive reagent and not easily available. The inventors of the present invention tried various combinations of proteolytic enzymes. It was found by the inventors of the present invention that a mixture of polypeptides treated with trypsin followed by treatment with carboxypeptidase B provides results similar to that of carboxypeptidase P.

OBJECT OF THE INVENTION

An object of the present invention is to provide molecular weight markers and use thereof in determining the molecular weight of Glatiramer acetate batches by GPC.

Another object of the present invention is to provide a simple, cost effective, commercially viable and consistent process for the preparation of polypeptides, in particular Glatiramer acetate.

Another object of the present invention is to provide a process for the preparation of trifluoroacetyl copolymer by treating the protected copolymer with about 7% to 20% HBr to obtain copolymer-1.

Yet another object of the present invention is to provide a process for the preparation of Copolymer-1 (Glatiramer acetate) by treating protected copolymer or trifluoroacetyl copolymer with dialkylamine selected from diethylamine, dimethylamine, or diisopropylamine, preferably diethylamine to obtain partially deprotected copolymer or completely deprotected copolymer.

Another object of the present invention is to provide a process for preparation of Glatiramer acetate where the wet solid obtained after the first deprotection step is not subjected to drying and is used as such for the further reaction which saves considerable time and hence is considered to be an industrially viable process.

Another object of the present invention provides a method of characterizing a polypeptide mixture, in particular Glatiramer acetate using trypsin and carboxypeptidase B.

SUMMARY OF THE INVENTION

The present invention provides a process for preparation of polypeptide fractions with random amino acid sequence similar to that of Glatiramer acetate, which serve as molecular weight markers for Glatiramer acetate, comprising the steps of,
  a) subjecting a polypeptide mixture, which is similar to Glatiramer acetate in terms of amino acid composition and molar ratio of amino acids, to Gel Permeation Chromatography (GPC)/Size Exclusion Chromatography (SEC) to obtain polypeptide fractions having molecular weights in the range of 2 kD to 30 kD;
  b) selecting polypeptide fractions to be used as molecular weight markers from said polypeptide fractions obtained in step a) in such a way that one of the fractions represent the peak apex molecular weight and other fractions are distributed on either side of the peak apex molecular weight; and
  c) determining tailing factor of these selected polypeptide fractions.

Preferably, tailing factor of selected polypeptide fractions is in the range of 0.8 to 1.

Preferably, polydispersity of said selected polypeptide fractions is less than or equal to 1.20.

Preferably, polypeptide mixture is Glatiramer acetate.

Another aspect of the present invention provides the use of polypeptide fractions, obtained by the process of the present invention, as molecular weight markers for determining the molecular weight of Glatiramer acetate batch by a process comprising the steps of,
  a) calibrating the SEC-HPLC column using said selected polypeptide fractions;
  b) establishing a relationship between retention time and log molecular weight of these selected fractions by means of a calibration curve;
  c) subjecting Glatiramer acetate batch whose molecular weight is to be determined to SEC-HPLC to obtain the retention time;
  d) using the relationship between the retention time and log molecular weight to determine the molecular weight of Glatiramer acetate batch.

Preferably, SEC-HPLC column is selected from Superose-12 or Superdex-75; mobile phase is selected from 0.1 to 0.3 M ammonium acetate or ammonium formate; and the flow rate is adjusted in the range of 0.4 to 0.6 ml/min.

Another aspect of the present invention provides a method of testing the consistency and reproducibility of the process for preparation of molecular weight markers, the method comprising the steps of,
  a) obtaining multiple set of molecular weight markers, using the process of present invention, from different batches of Glatiramer acetate/Copaxone, each set containing molecular weight markers having molecular weight in the range of 2000 to 13000 daltons;
  b) assigning molecular weight markers from each set obtained in step a) using statistical process of randomization to further generate a larger set of molecular weight markers; and
  c) using these larger sets obtained in step b) as molecular weight markers to determine the molecular weight of a Copaxone/Glatiramer acetate batch by GPC.

Preferably, molecular weight markers used in step c) provide predictable results based on 95% confidence interval.

Preferably, Glatiramer acetate used for the preparation of molecular weight markers is prepared by a process comprising the steps of,
  a) treating protected copolymer with about 7% to 20% HBr in acetic acid at about 25° C. for about 21-23 hours to obtain trifluoroacetyl copolymer;

b) treating said trifluoroacetyl copolymer with diethylamine to obtain completely deprotected copolymer;
c) converting completely deprotected copolymer to Glatiramer acetate.

Another aspect of the present invention provides process for preparation of Glatiramer acetate comprising the steps of,
a) treating protected copolymer with about 7% to 20% HBr in acetic acid at about 25° C. for about 21-23 hours to obtain trifluoroacetyl copolymer;
b) treating said trifluoroacetyl copolymer with a base selected from diethylamine, dimethylamine or diisopropylamine to obtain completely deprotected copolymer;
c) converting completely deprotected copolymer to Glatiramer acetate.

Preferably, the treatment in step a) is carried out at 25° C.±0.2° C.; said HBr in acetic acid is optionally pre-treated with a scavenger selected from phenol, resorcinol, tyrosine, sodium bisulfite, sodium thiosulphate, naphthalene, 1-naphthol or 2-naphthol; and said base is selected from diethylamine.

Another aspect of the present invention provides conversion of completely deprotected copolymer to Glatiramer acetate comprising the steps of,
a) concentrating an aqueous solution of completely deprotected copolymer to minimum volume using Tangential Flow Filtration (TFF) by passing through a cassette of polyether sulphone membrane having molecular weight cut off (MWCO) of 1 KD;
b) washing the concentrated solution of step a) with water till pH 8 to 9 is achieved followed by washing with 0.3% acetic acid solution for salt exchange to get Glatiramer acetate; and
c) washing Glatiramer acetate obtained in step b) with water till pH 5.5 to 7 is achieved to get pure Glatiramer acetate.

Preferably, Glatiramer acetate obtained by the process of the present invention has brominated tyrosine content not more than 0.15% and diethylamide content not more than 5000 ppm. Preferably, Glatiramer acetate obtained by the process of the present invention has an average molecular weight in the range of 5000-9000 Daltons.

Preferably, Glatiramer acetate obtained by the process of the present invention is used in the preparation of pharmaceutical composition either as a lyophilized solid or as an aqueous solution containing Glatiramer acetate in the concentration range of about 25-45 mg/ml.

Another aspect of the present invention provides process for characterization of Glatiramer acetate by peptide mapping using trypsin and carboxypeptidase B comprising the steps of,
a) enzymatic treatment of Glatiramer acetate using trypsin to obtain peptide fragments of short chain lengths;
b) treating the obtained peptide fragments with carboxypeptidase B resulting in further fragmentation of peptide chain;
c) separating and analyzing the peptide fragments obtained in step b) using HPLC-UV to obtain the chromatogram; and
d) comparing the chromatogram thus obtained with the chromatogram of reference standard to determine the structural similarity.

Preferably, the reference standard used for peptide mapping is Copaxone® (marketed formulation).

DETAILED DESCRIPTION OF THE INVENTION

Figure 1:
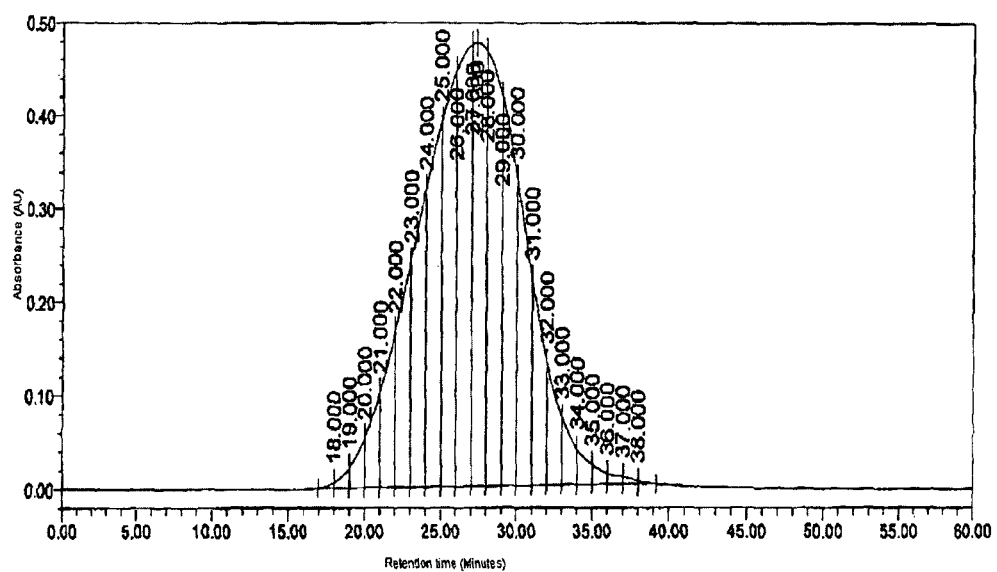
FIG. 1: Graph showing fractionation of Copaxone® batch no. P53289.

The present invention provides molecular weight markers for determining the molecular weight of polypeptides, in particular Glatiramer acetate (Copolymer-1).

Molecular weight markers used in the present invention are polypeptide fractions consisting of polypeptides with random amino acid sequence similar to that of Glatiramer acetate. Preferably, these molecular weight markers contain alanine, glutamic acid, tyrosine and lysine in the same molar ratio as present in Glatiramer acetate.

One embodiment of the present invention provides polypeptide fractions with random amino acid sequence similar to that of Glatiramer acetate, which serve as molecular weight markers for Glatiramer acetate, prepared by a process comprising the steps of,
a) subjecting a polypeptide mixture which is similar to Glatiramer acetate in terms of amino acid composition and molar ratio of amino acids to Gel Permeation Chromatography (GPC)/Size Exclusion Chromatography (SEC) to obtain polypeptide fractions having molecular weights in the range of 2 kD to 30 kD;
b) selecting polypeptide fractions to be used as molecular weight markers from said polypeptide fractions obtained in step a) in such a way that one of the fractions represent the peak apex molecular weight and other selected fractions are distributed on either side of the peak apex molecular weight; and
c) determining tailing factor of these selected polypeptide fractions.

Preferably, the tailing factor of these selected polypeptide fractions is in the range of 0.8 to 1. Peak symmetry as measured by, tailing factor is of great importance in chromatographic analysis. When the tailing factor increases, integration becomes less reliable.

Tailing factor can be calculated as per the USP method.

Preferably, polydispersity of these selected polypeptide fractions is less than or equal to 1.20.

Another embodiment of the present invention provides a process for preparation of polypeptide fractions with random amino acid sequence similar to that of Glatiramer acetate, which serve as molecular weight markers for Glatiramer acetate, comprising the steps of,
a) subjecting a polypeptide mixture which is similar to Glatiramer acetate in terms of amino acid composition and molar ratio of amino acids to Gel Permeation Chromatography (GPC)/Size Exclusion Chromatography (SEC) to obtain polypeptide fractions having molecular weights in the range of 2 kD to 30 kD;

b) selecting polypeptide fractions to be used as molecular weight markers from said polypeptide fractions obtained in step a) in such a way that one of the fractions represent the peak apex molecular weight and other selected fractions are distributed on either side of the peak apex molecular weight; and c) determining tailing factor of these selected polypeptide fractions.

Preferably, the tailing factor of these selected polypeptide fractions is in the range of 0.8 to 1. Polydispersity of these selected polypeptide fractions is preferably less than or equal to 1.20.

Preferably, the polypeptide mixture is Copaxone® or Glatiramer acetate obtained by the process of the present invention or by any other known process.

Column used in the chromatographic technique is selected from Superose-12 or Superdex-75, preferably Superose-12. Mobile phase is selected from ammonium acetate or ammonium formate. Ammonium acetate or ammonium formate is used in concentration range of 0.1 to 0.3M, preferably 0.2M. The pH of the mobile phase is about 4 to 6, preferably 5. The flow rate and amount of Copaxone®/Glatiramer acetate solution to be loaded on to the column depends on the radius and length of the column. Detectors used for the chromatographic technique are selected from UV detector, refractive index detector, MALLS, fluorescence detector or combination thereof.

Figure 3:
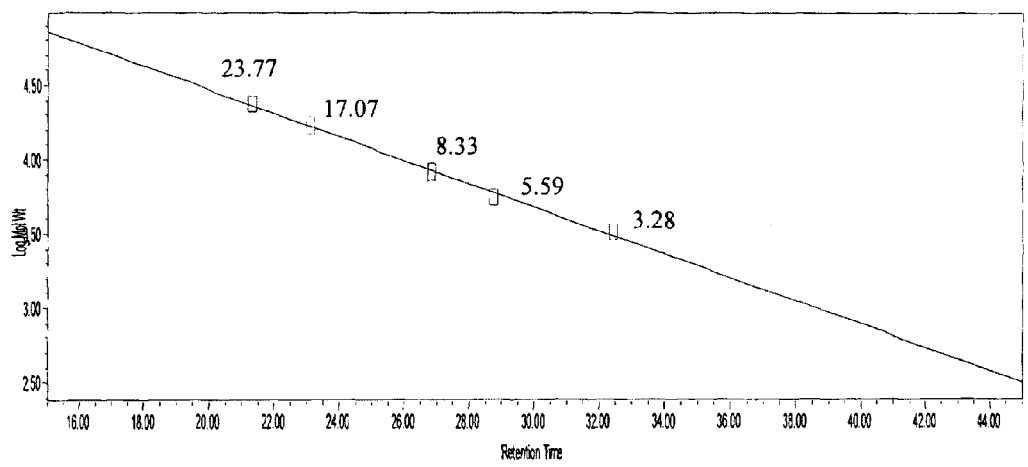
FIG. 3: Calibration curve of fractionated molecular weight markers.

In a preferred embodiment of the present invention, Copaxone®/Glatiramer acetate about 0.5 to 4 mg, preferably 2 mg is subjected to GPC (SEC) on a Superose-12 or Superdex-75 column using 0.2M ammonium formate, or ammonium acetate pH 5.0 as mobile phase. 22 individual fractions are collected in an interval gap of 1 minute as in FIG. 1. All fractions are lyophilized separately. Out of the 22 fractions, five fractions are selected in such a way that two from each side of the peak apex and the peak apex fraction are selected. The tailing factor of these polypeptide fractions is determined. The tailing factor is preferably in the range of 0.8 to 1. These selected fractions are suspended in 0.2M ammonium acetate or ammonium formate pH 5.0 and the final concentration of each of these fractions is made to 1-10 mg/ml, preferably 6 mg/ml. Molecular weight of these selected fractions are determined using SEC-MALLS. Mp (Peak apex molecular weight), Mw (Weight-average molecular weight), Mn (Number-average molecular weight) and polydispersity of each selected fraction are determined. Nearly identical values of Mp, Mw and Mn suggest that these fractions are almost monodisperse. Polydispersity of these fractions are less than 1.05. These characterized fractions are used as molecular weight markers for the determination of Mp, Mw and Mn of Glatiramer acetate batches. Each of these polypeptide fractions consists of polypeptide with random amino acid sequence. Calibration curve is plotted using the log molecular weight and retention time of these fractions as shown in FIG. 3. Correlation coefficient ($R^2$) for the calibration curve is 0.996.

SEC-HPLC conditions used for fractionation of Copaxone® are as provided in Table 1 below,

TABLE 1

Chromatographic conditions for SEC-HPLC

| | |
|---|---|
| HPLC | Waters HPLC |
| Detectors | UV, RI and MALLS |
| Software | Empower 2 and Astra |
| Column | Superose 12 (10/300 GL) or Superdex-75 |
| Mobile Phase | 0.2M Ammonium acetate pH 5.0 or 0.2M Ammonium formate pH 5.0 |
| Flow rate | 0.5 ml/min. |
| UV detection | 275 nm |
| RI conditions | Sensitivity: 32, Temp. : 30° C. |
| MALLS | Wyatt MiniDawn Treos |

Mp (Peak apex molecular weight), Mw (Weight-average molecular weight) and Mn (Number-average molecular weight) for the selected fraction are provided in Table 2 below,

TABLE 2

Characterized Fractions used as molecular weight markers

| Fraction | Mp (kD) | Mw (kD) | Mn (kD) | Polydispersity PD = Mw/Mn |
|---|---|---|---|---|
| Fraction # 5 | 23.77 | 23.88 | 23.76 | 1.01 |
| Fraction # 7 | 17.07 | 17.16 | 17.07 | 1.01 |
| Fraction # 11 | 8.33 | 8.82 | 8.62 | 1.02 |
| Fraction # 13 | 5.59 | 5.98 | 5.83 | 1.03 |
| Fraction # 17 | 3.28 | 3.48 | 3.43 | 1.01 |

The polydispersity index (PDI) is a measure of the distribution of molecular mass in a given polymer sample. It is calculated by dividing weight average molecular weight by the number average molecular weight. Nearly identical values of Mp, Mw and Mn suggest that these fractions are almost monodisperse.

In another preferred embodiment of the present invention, Glatiramer acetate about 40 mg is subjected to GPC on a Superose-12 (10/300) GL system using 0.2M ammonium acetate pH 5.0 as mobile phase. Glatiramer begins to elute after 20 minutes. About 30 fractions are collected at an interval of 0.5 min. 12 to 15 fractions are selected. These fractions are analyzed for tailing factor, molecular weight and polydispersity. Fractions are selected in such a way that one of these fractions represents the peak apex molecular weight and other fractions are distributed on either side of the peak apex molecular weight. Fractions having polydispersity of less than 1.2 are selected and lyophilized. Fractions having polydispersity of more than 1.2 are subjected to further purification so as to obtain fractions having polydispersity less than 1.2. Preferably fractions having molecular weight 3 kD, 5 kD, 7 kD, 10 kD and 12 kD are selected to be used as molecular weight markers.

GPC conditions used for fractionation of Glatiramer acetate prepared by the process of the present invention are provided in Table 3 below,

TABLE 3

Chromatographic conditions for Gel Permeation Chromatography

| | |
|---|---|
| System | Actapurifier |
| Column | Superose 12 (10/300 GL) |
| Mobile Phase | 0.2M Ammonium acetate pH 5.0 |
| Injection volume | 1 ml |
| Flow rate | 0.5 ml/min. |
| Total run time | 60 min |
| Detector | UV |
| UV detection | 280 nm |

Molecular weight of these selected fractions are determined using SEC-MALLS. Mp and polydispersity of these selected fractions are shown in Table 4 below,

TABLE 4

Characterized Fractions used as molecular weight markers

| Fraction | Mp(kD) | Polydispersity PD = Mw/Mn |
|---|---|---|
| Fraction # 16 | 12.56 | 1.05 |
| Fraction # 18 | 10.05 | 1.08 |
| Fraction # 22 | 7.38 | 1.17 |
| Fraction # 24 | 5.06 | 1.11 |
| Fraction # 26 | 3.2 | 1.05 |

Any number of fractions can be selected to be used as markers. The criteria for selection is that one of the fractions must represent peak apex molecular weight and other fractions which are selected must be distributed on either side of the peak apex molecular weight.

Preferably, the tailing factor of these selected fractions is in the range of 0.8 to 1.

These selected polypeptide fractions to be used as molecular weight markers are further characterized by NMR and amino acid ratio. The process for preparation of molecular weight markers as per the present invention is consistent and reproducible. The molecular weight markers obtained by the process of the present invention mimic Glatiramer acetate in terms of hydrodynamic volume.

Another embodiment of the present invention provides use of selected polypeptide fractions which serve as molecular weight markers for determining the molecular weight of a Glatiramer acetate batch, by a process comprising the steps of,
  a) calibrating the SEC/GPC column using selected polypeptide fractions;
  b) establishing a relationship between retention time and log molecular weight of these selected fractions by means of a calibration curve;
  c) subjecting Glatiramer acetate batch whose molecular weight is to be determined to SEC/GPC to obtain the retention time;
  d) using the relationship between the retention time and log molecular weight to determine the molecular weight of Glatiramer acetate batch.

Another embodiment of the present invention provides a process for determining the molecular weight of a Glatiramer acetate batch using the selected polypeptide fractions which serve as molecular weight markers, comprising the steps of,
  a) calibrating the SEC/GPC column using selected polypeptide fractions;
  b) establishing a relationship between the retention time and log molecular weight of these polypeptide fractions by means of a calibration curve;
  c) subjecting a Glatiramer acetate batch whose molecular weight is to be determined to SEC/GPC to obtain the retention time;
  d) using the relationship between the retention time and log molecular weight to determine the molecular weight of Glatiramer acetate batch.

Preferably, the peak apex molecular weight of Glatiramer acetate is determined.

Figure 4:
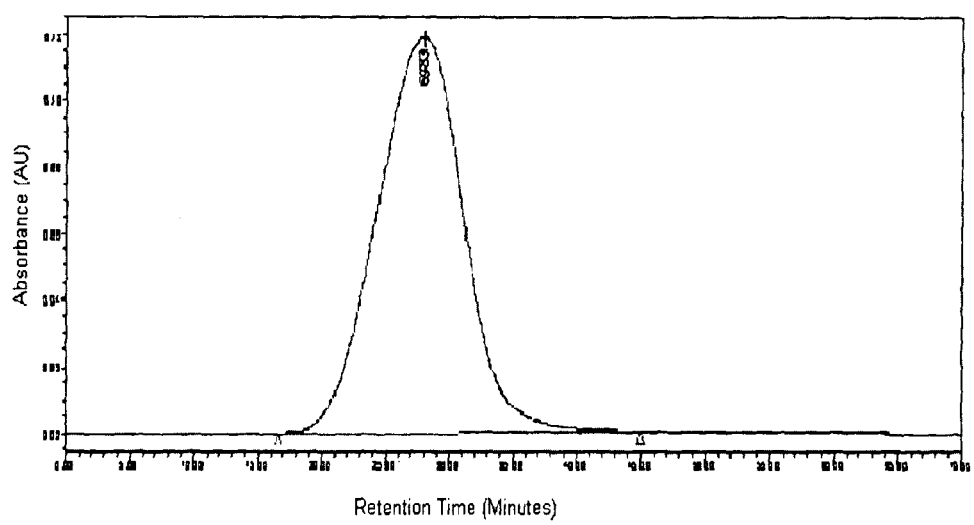
FIG. 4: Molecular weight determination of Copaxone® batch no. 53119 by GPC using fractionated molecular weight markers.

In a preferred embodiment, peak apex molecular weight of Glatiramer acetate is determined by SEC-HPLC using molecular weight markers mentioned herein. SEC-HPLC column is calibrated using selected polypeptide fractions which serve as molecular weight markers as mentioned herein. A relationship between the retention time and log molecular weight of these molecular weight markers is established by plotting a calibration curve as shown in FIG. 3. Copaxone®/Glatiramer acetate is subjected to SEC-HPLC on a Superose-12 or Superdex-75 column, preferably Superose-12 (10×300 mm) using 0.2M ammonium formate or ammonium acetate pH 5.0, preferably ammonium acetate as mobile phase. Injection volume of 50 µl sample having a concentration of about 2 mg/ml is loaded onto the column. Flow rate is maintained at 0.5 ml/min and the total run time is 60 min. The peak apex molecular weight is determined using UV detector at wavelength of 275 nm. Using the standard curve, two batches of Copaxone® and Glatiramer acetate are analyzed as shown in FIG. 4, using the molecular weight markers mentioned in Table 2 above and the results are as shown in Table 5 below:

TABLE 5

Molecular weight of Copaxone/Glatiramer acetate batches using the molecular weight markers mentioned in Table 2 above (Calibration curve):

| Batch No. | Mp (kDa) | Mw (kDa) | Mn (kDa) |
|---|---|---|---|
| Example 7 | 7.98 | 8.76 | 5.91 |
| Example 8 | 7.73 | 8.87 | 6.1 |
| Cop.# 53119 | 6.98 | 8.46 | 5.98 |
| Cop.# 53289 | 7.87 | 9.55 | 6.55 |

The test results for GPC of COPAXONE® using molecular weight markers mentioned in Table 2 above, are as summarized in Table 6 below:

TABLE 6

GPC of COPAXONE

| COPAXONE ® Lot no. | $M_p$ [D] |
|---|---|
| 538490 | 7571 |
| P53131 | 7892 |
| 538518 | 7514 |
| P53119 | 6983 |
| P53289 | 7870 |
| P53630 | 7579 |
| P53631 | 7566 |
| P53313 | 7025 |
| P53154 | 6535 |
| P53613 | 7130 |

Figure 7:
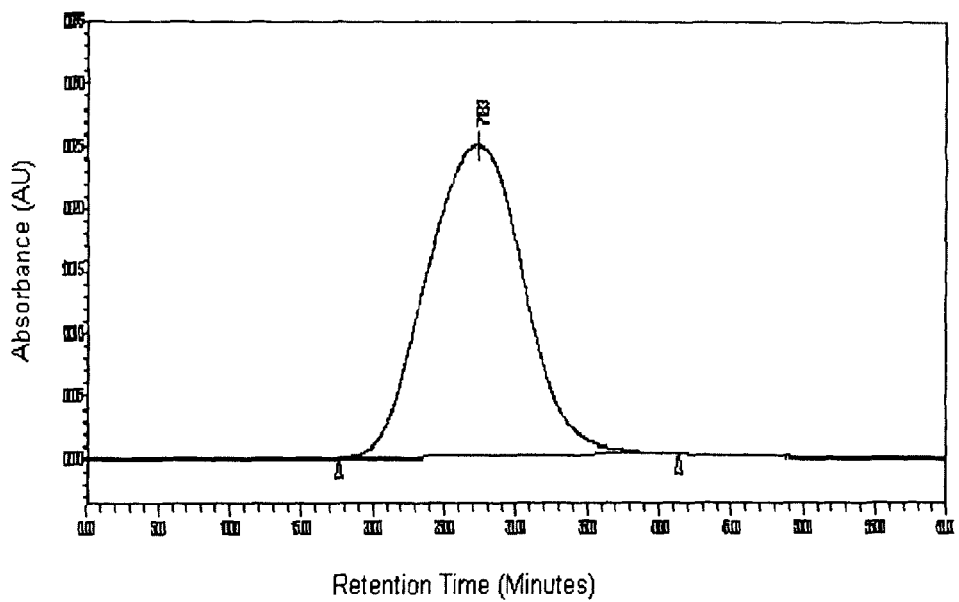
FIG. 7: Molecular weight determination of Glatiramer acetate using the markers provided in Table 4.

Two batches of Copaxone® and Glatiramer acetate are analyzed as shown in FIG. 7, using the molecular weight markers mentioned in Table 4 above and the results are as shown in Table 7 below:

TABLE 7

Molecular weight of Copaxone/Glatiramer acetate batches using the molecular weight markers mentioned in Table 4 above (Calibration curve):

| Batch No. | Mp (kD) |
|---|---|
| Glatiramer acetate obtained by process of present invention | 7275 |
| Glatiramer acetate obtained by process of present invention | 7234 |
| P53313 | 7183 |
| P53289 | 7571 |

Copaxone/Glatiramer acetate batches analyzed by this method shows an average molecular weight between 5000-9000 Daltons.

Glatiramer acetate batch, molecular weight of which is determined using the above method can be used for the preparation of molecular weight markers as mentioned herein.

Another embodiment of the present invention provides a method for testing the consistency and reproducibility of the process for preparation of molecular weight markers by using statistical techniques.

The method involves the following steps:
a) obtaining multiple set of molecular weight markers, using the process of present invention, from different batches of Glatiramer acetate/Copaxone, each set containing molecular weight markers having molecular weight in the range of 2000 to 13000 daltons;
b) assigning molecular weight markers from each set obtained in step a) using statistical process of randomization to further generate a larger set of molecular weight markers; and
c) using these larger sets obtained in step b) as molecular weight markers to determine the molecular weight of a Copaxone/Glatiramer acetate batch by GPC.

In a preferred embodiment, five sets of molecular weight markers are generated using different batches of Glatiramer acetate. Each set contains seven molecular weight markers having different molecular weights in the range of 2000 to 13000 daltons, as shown in Table 8 below,

TABLE 8

| Set 1 | Set 2 | Set 3 | Set 4 | Set 5 |
|---|---|---|---|---|
| 12628 | 12208 | 12215 | 12373 | 12580 |
| 9892 | 9241 | 9915 | 10128 | 8939 |
| 7019 | 7991 | 6706 | 7870 | 6556 |
| 6185 | 6335 | 6073 | 6267 | 5890 |
| 5163 | 5704 | 5532 | 5631 | 4969 |
| 4888 | 4612 | 4755 | 4000 | 4069 |
| 2709 | 2989 | 3775 | 3292 | 3671 |

Statistical process of randomization is applied to these five sets of molecular weight markers to generate a larger set of molecular weight markers, each set containing seven molecular weight markers as in Table 9 below,

TABLE 9

| 1 | 2 | 3 | 4 | 5 | 6 | 7 | 8 | 9 | 10 |
|---|---|---|---|---|---|---|---|---|---|
| 12215 | 12628 | 12373 | 12628 | 12215 | 12215 | 12215 | 12373 | 12373 | 12628 |
| 8939 | 10128 | 9241 | 8939 | 10128 | 9892 | 9892 | 9915 | 9915 | 9915 |
| 7991 | 6556 | 7991 | 7991 | 6556 | 7991 | 6706 | 6706 | 6706 | 6556 |
| 6267 | 6073 | 6335 | 6073 | 6267 | 6073 | 5890 | 5890 | 6267 | 6185 |
| 4969 | 5163 | 5704 | 5532 | 5704 | 4969 | 5532 | 5704 | 4969 | 4969 |
| 4755 | 4069 | 4069 | 4069 | 4000 | 4755 | 4612 | 4755 | 4755 | 4755 |
| 2989 | 3775 | 2989 | 2709 | 2989 | 2989 | 3671 | 3775 | 3671 | 3292 |

These larger sets of markers are then used to determine the peak apex molecular weight of Glatiramer acetate batch and the results are as shown below in table 10,

TABLE 10

| Batch No. | Min | Max | Diff | Mean | SD | RSD | Confidence interval (95% level) |
|---|---|---|---|---|---|---|---|
| Batch 1 | 6811 | 7108 | 297 | 6916 | 95.00 | 1.37 | 6971 |
| Batch 2 | 6739 | 7036 | 297 | 6842 | 95.61 | 1.40 | 6897 |
| Batch 3 | 6763 | 7060 | 297 | 6867 | 95.37 | 1.39 | 6922 |

This randomization study reveals that any permutation-combination of molecular weight markers taken from different sets will provide predictable results based on 95% confidence interval. This indicates that the process of the present invention for preparation of molecular weight markers is consistent, reproducible and is not affected by batch to batch variation of the starting material. Molecular weight markers generated using the process of present invention from different batches of Glatiramer acetate provides predictable results based on 95% confidence interval.

In an alternate embodiment of the present invention, molecular weights of Glatiramer acetate can be determined by using Glatiramoids as molecular weight markers. Glatiramoids are heterogenous polypeptide mixture comprising the four amino acids, L-Glutamic acid, L-Alanine, L-Lysine and L-Tyrosine in the same molar ratio as Glatiramer. Glatiramoids of various molecular weights are obtained by quenching the reaction mixture at various time intervals during HBr-acetic acid deprotection stage followed by deprotection using amines such as diethylamine, dimethylamine, diisopropylamine or piperidine, preferably diethylamine.

Another embodiment of the present invention provides an improved process for the preparation of polypeptides, particularly Glatiramer acetate also known as Copolymer-1, with average molecular weight of 5000-9000 Daltons, from amino acids, namely, L-tyrosine, L-alanine, L-glutamic acid and L-lysine or pharmaceutically acceptable salt thereof.

According to one embodiment of the present invention there is provided a process for preparing copolymer-1 (Glatiramer acetate) with an average molecular weight of 5000-9000 daltons comprising:
a) treating protected copolymer with about 7% to 20% HBr in acetic acid at about 25° C. for about 21-23 hours to obtain trifluoroacetyl copolymer;
b) treating said trifluoroacetyl copolymer with a base to obtain completely deprotected copolymer;
c) converting completely deprotected copolymer to Copolymer 1.

Protected copolymer is obtained by polymerizing a mixture of N-carboxyanhydride of L-alanine, N-carboxyanhydride of γ-protected L-glutamate, N-carboxyanhydride of ε-N-protected L-lysine and N-carboxyanhydride of L-tyrosine in presence of an initiator to get the protected copolymer. The protecting group (PG) for the free γ-carboxy group of L-glutamic acid is selected from substituted or unsubstituted alkyl, aryl or aralkyl group, preferably benzyl group or substituted benzyl group and the protecting group (PG) for the free ε-amino group of L-lysine is selected from acyl or substituted acyl where the substituents are selected from alkyl, aryl or halo, preferably trifluoroacetyl group.

In a preferred embodiment of the present invention, a mixture of N-carboxyanhydride of L-alanine, N-carboxyanhydride of γ-benzyl L-glutamate, N-carboxyanhydride of $N^\epsilon$-trifluoroacetyl L-lysine and N-carboxyanhydride of L-tyrosine, is dissolved in a suitable solvent, preferably anhydrous dioxane over a period of 1 hour, preferably 30 min, more preferably 15 min. To this mixture, 1% diethylamine in anhydrous dioxane is added in one lot. The reaction mixture is stirred at room temperature for 24 hrs at 200-215 rpm. After the completion of reaction, deionized water is added to the reaction mixture to get the protected copolymer as a white solid. The obtained solid is filtered under vacuum, washed with deionized water and dried till loss on drying (LOD) NMT 10% is achieved. Protected copolymer is treated with about 7% to 20% of hydrogen bromide (HBr), preferably about 15% HBr in acetic acid and the mixture is stirred at about 25° C., preferably at 25° C.±0.2° C. for about 21-23 hours at 200-215 rpm to obtain trifluoroacetyl copolymer. The reaction mixture is then poured into ice cold water to get a white solid which is then neutralized by treating with ammonia solution till pH 6-7 is achieved and is stirred for 24 hr. The solid is filtered and washed with water. This treatment of the obtained solid suspension with ammonia solution also decomposes benzyl bromide which is generated during the reaction.

The partially deprotected copolymer, trifluoroacetyl copolymer thus obtained is converted to Glatiramer acetate by the process disclosed in our pending Indian Patent Application 1082/MUM/2009 dated 23 Apr. 2009 or by any other known method.

The prior art describes the removal of benzyl protection group of glutamic acid by using 33% hydrogen bromide in acetic acid. Use of 33% HBr-acetic acid (harsh conditions for peptides) can lead to inconsistent and random cleavage of the peptide bonds in the polymer which on further deprotection results in Glatiramer acetate having inconsistent molecular weight. The process of the present invention employs the use of about 7% to 20% HBr, preferably about 15% at about 25° C. for about 21-23 hours for the removal of the benzyl protecting group, which on further deprotection results in Glatiramer acetate having molecular weights which are consistent and reproducible.

According to another embodiment of the present invention, about 7% to 20% HBr, preferably about 15% HBr in acetic acid is taken in a temperature controlled reactor at room temperature and stirred at 200-215 rpm for 20-60 minutes, preferably 30 minutes until about 25° C. is reached. Scavenger is added to the reaction mixture and stirred for 1-3 hours, preferably for 2 hours at room temperature, preferably at about 25° C. at 200-215 rpm followed by addition of protected copolymer in to the reactor and stirring at room temperature, preferably at about 25° C., more preferably at 25° C.±0.2° C. at 200-215 rpm for 20-25 hours, preferably 21-23 hours. The reaction mixture is quenched in cold water to obtain white solid followed by addition of ammonia solution till pH of 6-7 is achieved and is stirred for 24 hr. The obtained solid, trifluoroacetyl copolymer is filtered, washed with water and air dried. Scavenger used to reduce the free bromine content are selected from phenol, resorcinol, tyrosine, sodium bisulfate, sodium thiosulphate, naphthalene, 1-naphthol or 2-naphthol, preferably phenol or resorcinol.

Another embodiment of the present invention provides a process for preparation of Glatiramer acetate which comprises subjecting the protected copolymer to particle size reduction, so as to obtain uniformity in particle size, prior to deprotection. This ensures consistency and reproducibility in molecular weights of Glatiramer acetate batches. In a preferred embodiment, protected copolymer is passed through 30 mesh sieve so as to obtain uniform particle size.

Another embodiment of the present invention provides a process for preparation of Copolymer-1 (Glatiramer acetate) which comprises treating protected copolymer or trifluoroacetyl copolymer with dialkyl amine such as diethylamine, dimethylamine, diisopropylamine, preferably diethylamine to obtain partially deprotected copolymer or completely deprotected copolymer and converting the obtained partially deprotected copolymer or completely deprotected copolymer to Copolymer-1 (Glatiramer acetate).

In a preferred embodiment of the present invention, the partially deprotected copolymer, trifluoroacetyl copolymer is suspended in a suitable solvent, preferably water and treated with diethylamine followed by stirring for 20-30 hours, preferably 24 hours at room temperature. The reaction mixture is passed through 0.2µ filter, subjected to tangential flow filtration through a cassette having molecular weight cut off (MWCO) of 1 KD, diafiltered with deionized water until pH 8-9 is achieved, then with 0.3% aqueous acetic acid followed by washing with deionized water until pH 5.5-7.0 is achieved. The obtained solution is then lyophilized to obtain Copolymer-1 (Glatiramer acetate) with the desired molecular weight range. The obtained solid exhibits average molecular weight in the range of 5000 to 9000 Daltons as determined by GPC and MALLS. Alternatively, the above solution can be taken as such for formulation.

In the process of the present invention, diethylamine is used as an initiator as well as a deprotecting agent. Diethylamine, when used in smaller amounts in the range of 0.5% to 5% with respect to the NCAs of L-amino acids acts as an initiator and when used in higher amounts in the range of 1 to 5 times the weight of protected copolymer acts as a deprotecting agent for the removal of the $N^\epsilon$-trifluoroacetyl groups.

This reaction scheme is as shown in Scheme II below:

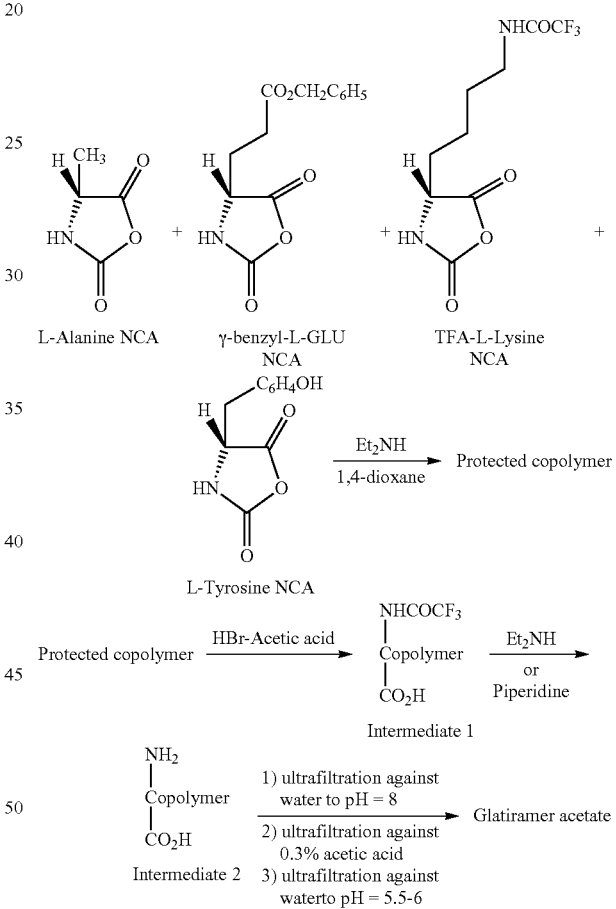

In another preferred embodiment of the present invention, the process for the preparation of Copolymer-1 (Glatiramer acetate) comprises the steps of,
a) polymerizing a mixture of N-carboxyanhydride of L-alanine, N-carboxyanhydride of γ-protected L-glutamate, N-carboxyanhydride of ε-N-protected L-lysine and N-carboxyanhydride of L-tyrosine in presence of initiator to get protected copolymer;
b) optionally treating the protected copolymer to obtain uniform particle size;
c) treating protected copolymer from step a) or b) with about 7% to 20% HBr, preferably about 15% HBr in acetic acid at room temperature, preferably at about 25° C., more preferably at 25° C.±0.2° C. for about 21-23 hr to obtain partially deprotected copolymer, trifluoroacetyl copolymer;

d) treating the obtained partially deprotected copolymer, trifluoroacetyl copolymer with diethylamine to obtain completely deprotected polymer;

e) subjecting completely deprotected copolymer to purification and salt exchange.

Preferably protected copolymer of uniform particle size can be obtained by passing protected copolymer through a sieve of desired mesh size, preferably 30 mesh sieve.

An alternate embodiment of the present invention provides a process for the preparation of Glatiramer acetate where the deprotection sequence is reversed comprising first treating the protected copolymer with diethyl amine to remove the trifluoroacetyl group and then with HBr/acetic acid to remove the benzyl group.

Another embodiment of the present invention provides a process for the preparation of Glatiramer acetate where the wet solid obtained after the first deprotection step is not subjected to drying and is used as such for the further reaction which saves considerable time and hence is considered to be an industrially viable process. The reaction scheme is as shown in Scheme III below,

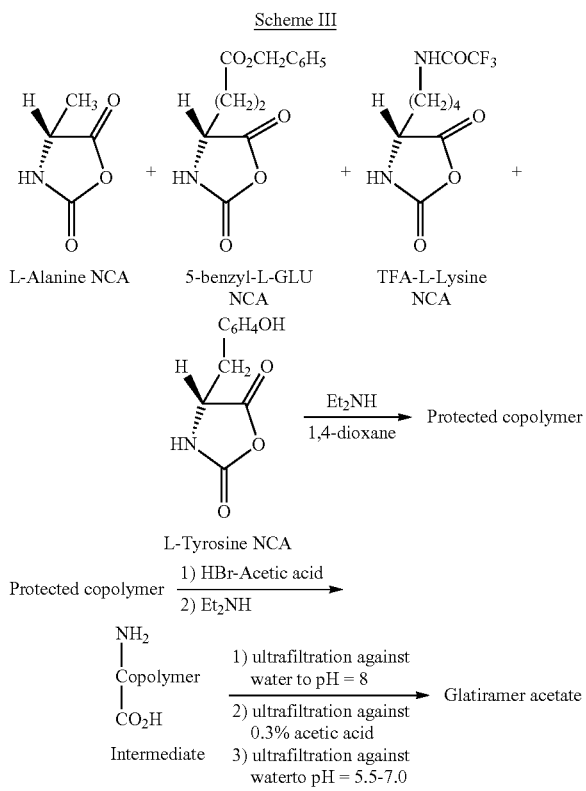

Scheme III

Another embodiment of the present invention provides process for purification and salt exchange of completely deprotected copolymer (Glatiramer) by ultrafiltration, comprising the steps of, a) concentrating an aqueous solution of completely deprotected copolymer (Glatiramer) to minimum volume using Tangential Flow Filtration (TFF) by passing through a cassette of polyether sulphone membrane having molecular weight cut off (MWCO) of 1 KD;

b) washing the concentrated solution of step a) with water till pH 8 to 9 is achieved followed by washings with 0.3% acetic acid solution for salt exchange to get Glatiramer acetate;

c) washing the obtained Glatiramer acetate with water till pH 5.5 to 7 is achieved to get pure Glatiramer acetate.

The water used for the above process is preferably RO (Reverse osmosis) water or WFI (water for Injection).

The undesired low molecular weight polypeptides formed during the process are removed by filtration. Filtration techniques employed, to remove the undesired molecular weight polypeptides can be selected from dialysis, ultrafiltration or tangential flow filtration.

Glatiramer acetate obtained by the process of the present invention has brominated tyrosine content not more than about 0.15% when tested by Reverse Phase-HPLC method and diethylamide content not more than about 5000 ppm, when tested by Ion Chromatography method.

N-carboxyanhydride (NCA) of L-amino acid such as L-tyrosine, L-alanine, protected L-glutamic acid and protected L-lysine can be prepared as disclosed in our pending Indian Patent Application 1082/MUM/2009 dated 23 Apr. 2009 or by any other known method.

Copolymer-1 (Glatiramer acetate) obtained according to the present invention, characterized by MALDI, IR, NMR, GPC, CD, UV and amino acid analysis (AAA), is found to be equivalent to COPAXONE®.

Glatiramer acetate, prepared by the present invention has an average molecular weight between 5000-9000 D and is substantially free of high molecular weight species having molecular weight equal to or greater than about 35 KD. Molecular weight of Glatiramer acetate obtained according to the present invention can be determined using the markers described herein.

Glatiramer acetate is a mixture of polypeptides composed of a mixture of Alanine, Glutamic acid, Lysine and Tyrosine in a molar ratio of approximately 4.6:1.5:3.6:1 respectively. The corresponding molar fractions are approximately 0.427 for alanine, 0.141 for glutamic acid, 0.338 for lysine and 0.095 for tyrosine, which may vary by about ±10%. The molar fractions of Amino Acid is determined by Ultra Performance Liquid Chromatography (UPLC) using AccQ.Tag Ultra Column (2.1×100 mm, 1.7 μm) and an UV detector. A gradient system is used as the mobile phase.

The molar fraction measured for innovator sample (COPAXONE®) and Copolymer-1 (Glatiramer acetate) prepared according to the present invention is found to be in the range mentioned in Table 11.

The standard molar fraction range for amino acids are summarized in Table 11:

| Amino Acids | Std. Molar fraction | Std. Molar fraction range |
| --- | --- | --- |
| L-Tyrosine | 0.095 | 0.085-0.104 |
| L-Glutamic Acid | 0.141 | 0.127-0.155 |
| L-Lysine | 0.338 | 0.304-0.372 |
| L-Alanine | 0.427 | 0.384-0.470 |

Yet another method for characterizing polypeptides is peptide mapping. It involves chemical or enzymatic treatment of polypeptide resulting in the formation of peptide fragments followed by separation and identification of the fragments in a reproducible manner. Peptide mapping is a comparative procedure, because the information obtained, compared to a reference material similarly treated, confirms the primary structure of the polypeptide. A peptide map may be viewed as a fingerprint of a protein/polypeptide.

Another embodiment of the present invention provides analytical method for characterization of polypeptides, in particular Glatiramer acetate using trypsin and carboxypeptidase B, comprising the steps of,
- a) enzymatic treatment of polypeptides in particular Glatiramer acetate using trypsin to obtain peptide fragments of short chain lengths;
- b) treating the peptide fragments obtained in step a) with carboxypeptidase B resulting in further fragmentation of the peptide chain;
- c) separating and analyzing the peptide fragments obtained in step b) using HPLC technique to obtain the chromatogram; and
- d) comparing the chromatogram thus obtained with the chromatogram of reference standard to determine the structural similarity.

Preferably, the reference standard is Copaxone® (marketed formulation).

In a preferred embodiment, Glatiramer acetate obtained by the present invention is subjected to enzymatic treatment using trypsin (treated with tosyl-L-phenyl alanine chloromethyl ketone) at a temperature of about 37° C. and pH of about 8. This treatment is continued for about 4 hours to obtain peptide fragments of short chain lengths. This mixture of peptide fragments obtained after trypsin treatment is subjected to carboxypeptidase B treatment at 37° C. for about 18 hours which results in further fragmentation of the peptide chain. These fragments are separated and analyzed on a C18, 250×4.6 mm HPLC column to obtain a chromatogram. Chromatogram thus obtained is compared with the chromatogram obtained by subjecting Copaxone® to the same treatment as mentioned above.

Figure 8:
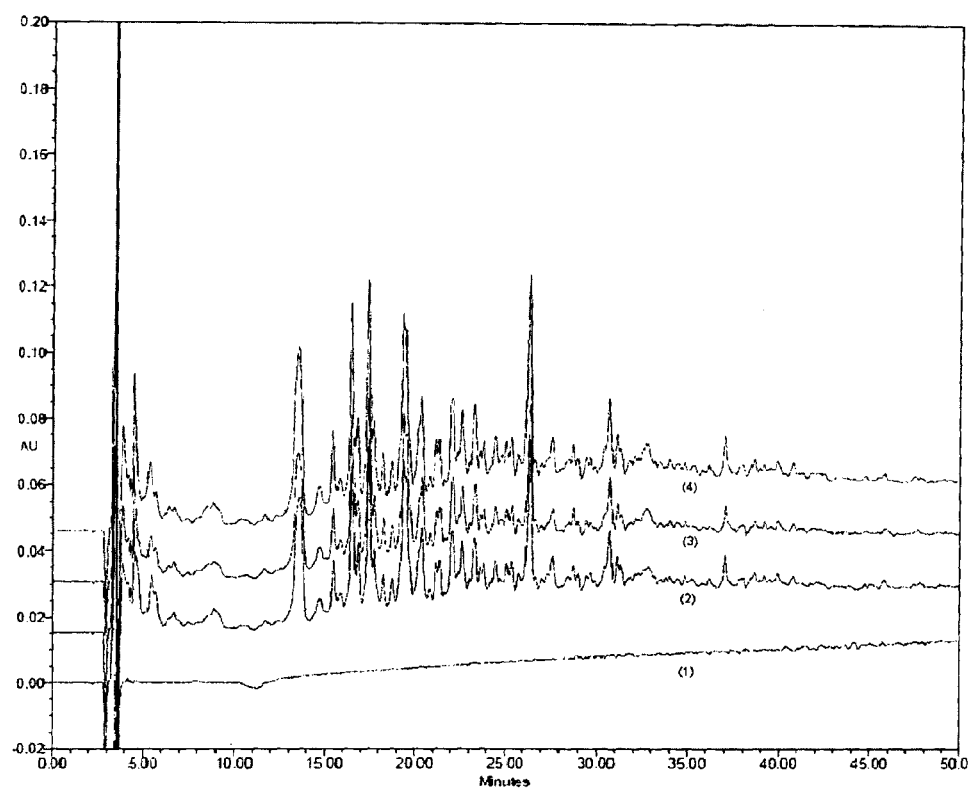
FIG. 8: Overlaid chromatogram comparing the cleavage pattern of Copaxone® and Glatiramer acetate, obtained by the process of the present invention, when treated with Trypsin enzyme.
Figure 9:
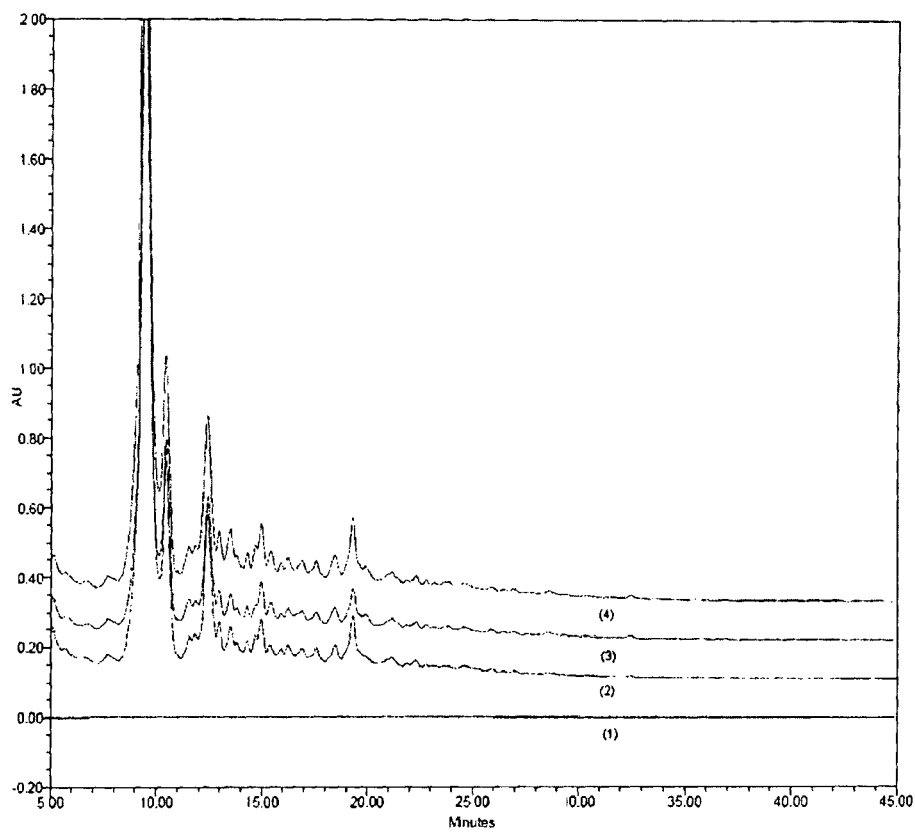
FIG. 9: Overlaid chromatogram comparing the cleavage pattern of Copaxone® and Glatiramer acetate, obtained by the process of the present invention, when treated with Trypsin followed by Carboxypeptidase B enzyme.

Overlaid chromatogram of Copaxone® batch 53378 and Glatiramer acetate batches obtained by the process of the present invention treated with trypsin alone is as shown in FIG. 8. Overlaid chromatogram of Copaxone® batch 53378 and Glatiramer acetate batches obtained by the process of the present invention treated with trypsin followed by carboxypeptidase B is as shown in FIG. 9. These chromatogram profiles indicate structural similarity between Copaxone and Glatiramer acetate batches, obtained by the process of the present invention.

In FIG. 8 and FIG. 9, (1) represents the blank solution; (2) represents the fragmentation pattern for reference standard .i.e., Copaxone® batch 53378; and (3) and (4) represent the fragmentation pattern for two batches of Glatiramer acetate obtained by the process of the present invention.

Prior art discloses the use of trypsin and carboxypeptidase P for peptide mapping of Glatiramer acetate. It has been found by the inventors of the present invention that Glatiramer acetate treated with trypsin followed by treatment with carboxypeptidase B provides a cleavage pattern similar to that of carboxypeptidase P. Carboxypeptidase B is selected over carboxypeptidase P due to its easy availability and cost effectiveness.

According to another embodiment, the invention provides pharmaceutical composition in the form of an injectable dosage form comprising an effective amount of glatiramer acetate; and a pharmaceutically acceptable tonicity agent.

According to a preferred embodiment, the invention provides pharmaceutical composition in the form of a subcutaneous injection comprising a unit dose of 1 ml of an aqueous solution comprising:
- a) 20 mg of glatiramer acetate; and
- b) 40 mg of mannitol.

According to another embodiment, the invention provides a process for preparing a pharmaceutical composition in the form of a subcutaneous injection comprising:

- a) providing concentrated solution of glatiramer acetate with concentration (assay) ranging from 25 mg/ml to 45 mg/ml;
- b) dissolving the tonicity agent in part quantity of water for injection to form a solution;
- c) adding the required quantity of concentrated solution of glatiramer acetate to solution of step (b);
- d) making up of the final volume of solution using Water for Injection;
- e) filtering the solution of step (d) through 0.2µ sterilizing grade filter to obtain filtered solution;
- f) filling said filtered solution into vials.

In a preferred embodiment, the invention provides a process for preparing a pharmaceutical composition in the form of a subcutaneous injection comprising:
- a) providing concentrated solution of glatiramer acetate with concentration (assay) ranging from 30 mg/ml to 40 mg/ml;
- b) dissolving mannitol in part quantity of water for injection;
- c) adding the required quantity of concentrated solution of glatiramer acetate to solution of step b);
- d) making up of the final volume of solution using Water for Injection;
- e) filtering the solution of step d) through 0.2µ sterilizing grade filter to obtain filtered solution;
- f) filling said filtered solution into vials.

According to another embodiment, the invention provides a process for preparing a pharmaceutical composition in the form of a subcutaneous injection comprising:
- a) providing glatiramer acetate;
- b) dissolving the tonicity agent in part quantity of water for injection to form a solution;
- c) dissolving glatiramer acetate in the solution of step b);
- d) making up of the final volume of solution using Water for Injection;
- e) filtering the solution of step d) through 0.2µ sterilizing grade filter to obtain filtered solution;
- f) filling said filtered solution into vials.

According to a preferred embodiment, the invention provides a process for preparing a pharmaceutical composition in the form of a subcutaneous injection comprising:
- a) providing glatiramer acetate;
- b) dissolving mannitol in part quantity of water for injection to form a solution;
- c) dissolving glatiramer acetate in the solution of step (b);
- d) making up of the final volume of solution using Water for Injection;
- e) filtering the solution of step (d) through 0.2µ sterilizing grade filter to obtain filtered solution;
- f) filling said filtered solution into vials.

Glatiramer acetate is used in the preparation of pharmaceutical composition either as a lyophilized solid or as an aqueous solution containing Glatiramer acetate in the concentration range of about 25-45 mg/ml.

Glatiramer acetate may be used in the range of about 1.0% to 4.0% by weight of total composition. Tonicity agents may be used in the range of about 0.9% to 9.75% by weight of total composition.

In the practice of the present invention, the tonicity agent that may be used includes but are not limited to sodium chloride, dextrose, mannitol, sucrose, lactose, galactose, trehalose, glycine or mixture thereof.

In the practice of the present invention, the composition of the present invention may be sterilized using membrane filters having pore size of about 0.2 microns. Suitable membrane filters that may be used include Polyvinylidene fluoride (PVDF), Polyethersulfone (PES) and cellulose acetate membrane.

Unless otherwise indicated, the following definitions are set forth to illustrate and define the meaning and scope of the various terms used to describe the invention herein.

The term "room temperature" should be understood to mean a temperature ranging from about 20° C. to about 40° C., preferably 25° C. to 35° C.

The term Glatiramer acetate will include Copaxone®, Glatiramer acetate prepared by the process of the present invention or prepared by any other process.

The term "copolymer-1" and "Glatiramer acetate" as used herein are synonymous.

The term "substantially free" as used herein means Glatiramer acetate containing less than about 0.2% of high molecular weight species having molecular weight equal to or greater than about 40 KD, preferably less than about 0.2% of 35 KD species, more preferably less than about 0.2% of 35 KD species and no detectable amounts of 40 KD species.

Initiators can be selected from bases, nucleophiles or combination thereof. In particular, initiator can include one or more amines, alcohols, water or combination thereof.

Amines employed may be primary, secondary or tertiary amine. Suitable amines include, but are not limited to, dimethylamine, diethylamine, di-n-propylamine, di-isopropylamine, di-secbutylamine, N-ethylmethylamine, di-n-butylamine, di-isobutylamine, di-tert-butylamine, diamylamine, di-n-octylamine, di-(2-ethylhexyl)amine, di-isononylamine, diallylamine, N-methylaniline, diphenylamine, or combination thereof, preferable being diethylamine. Other initiators which can be used for polymerization include K-tOBu, NaH, KH, triethylamine, tetramethylpiperidine, dicyclohexylamine, dicyclohexylundecane, lithium diisopropyl amine, t-BuLi or combination thereof. The initiator is used in an amount of about 0.2% to 4%, preferably 0.5 to 1.5%.

The suitable solvent used is selected from the group consisting of water, alcohol, polar aprotic solvent, chlorinated hydrocarbon or hydrocarbon. The preferred solvent used for deprotection is water. Alcohol can be selected from straight or branched chain alcohol. The polar aprotic solvent is selected from methyl acetate, ethyl acetate, dimethylfuran, dimethylformamide, 1,4-dioxane, tetrahydrofuran or mixture thereof. Chlorinated hydrocarbon can be selected from methylene dichloride, chloroform or ethylene dichloride. Hydrocarbon can be selected from hexane, pentane, cyclohexane and the like.

Other acids which may be used instead of HBr-acetic acid mixture can be selected from HCl, $H_2SO_4$, $HNO_3$, phosphorous acid, phosphoric acid, fluorosulfonic acid, chlorosulfonic acid, acetic acid, formic acid, propionic acid, benzene sulfonic acid, methane sulfonic acid, p-toluenesulfonic acid, p-(n-dodecyl)benzene sulfonic acid or combination thereof.

While the present invention has been described in terms of its specific embodiments, certain modifications and equivalents will be apparent to those skilled in the art and are included within the scope of the present invention. The examples are provided to illustrate particular aspects of the disclosure and do not limit the scope of the present invention.

EXAMPLES

Example 1(A)

Molecular Weight Determination of Glatiramer Acetate Batches a) Fractionation of Copaxone by SEC-HPLC:

SEC-HPLC was performed with Superose 12 (10/300 GL) column using 0.2M Ammonium acetate pH 5.0 as mobile phase, at a flow rate of 0.5 ml/min.

100 µL of Copaxone (B. No. P53289, 20 mg/mL) was injected on to the column as per the optimized method, making the final injected concentration as 2 mg.

Copaxone peak started eluting at around 17 min and ended at around 40 min.

22 individual fractions were collected within an interval gap of 1 minute (FIG. 1) starting from the $17^{th}$ minute and ending at the $39^{th}$ minute by using Waters HPLC and Autofraction collector.

All the 22 fractions collected separately were lyophilized completely.

b) Analysis of Fractionated Co-Polymer (Copaxone) by SEC-MALLS:

Chromatographic Conditions:

| HPLC | Waters HPLC |
|---|---|
| Detectors | UV, RI and MALLS |
| Software | Empower 2 and Astra |
| Column | Superose 12 (10/300 GL) |
| Mobile Phase | 0.2M Ammonium acetate pH 5.0 |
| Flow rate | 0.5 ml/min. |
| UV detection | 275 nm |
| RI conditions | Sensitivity: 32, Temp.: 30° C. |
| MALLS | Wyatt MiniDawn Treos |

Figure 2:
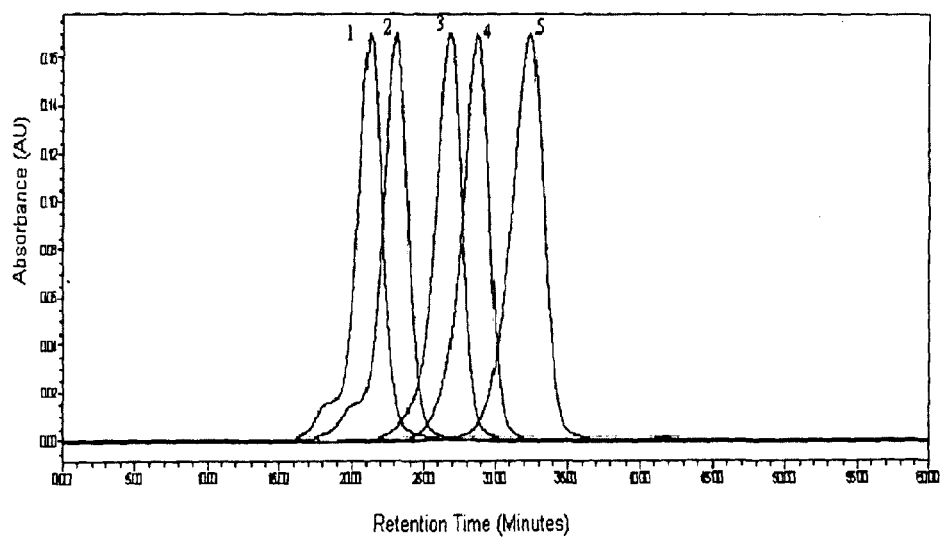
FIG. 2: Overlaid peak profile of selected fractions (molecular weight markers).

Two fractions each on either side of the peak apex and the fraction at the peak apex (Total: 5 fractions, FIG. 2) were taken for SEC-MALLS. These were resuspended in 0.2M Ammonium acetate pH 5.0 making the final concentration of each fraction to 6 mg/ml.

Analysis was performed to determine the Mp, Mw, Mn and Polydispersity of each fraction.

Results:

| Fraction | Mp (kDa) | Mw (kDa) | Mn (kDa) | Poly-dispersity |
|---|---|---|---|---|
| Fraction # 5 | 23.77 | 23.88 | 23.76 | 1.01 |
| Fraction # 7 | 17.07 | 17.16 | 17.07 | 1.01 |
| Fraction # 11 | 8.33 | 8.82 | 8.62 | 1.02 |
| Fraction # 13 | 5.59 | 5.98 | 5.83 | 1.03 |
| Fraction # 17 | 3.28 | 3.48 | 3.43 | 1.01 |

Identical values of Mp, Mw and Mn suggest that the fractionated samples were almost monodisperse. The polydispersity of fractionated samples were less than 1.05.

c) Use of Characterised Fractionated Co-Polymer as Molecular Weight Markers for the Determination of Mp, Mw and Mn of Glatiramer by Size Exclusion Chromatography (SEC):

Fractions 5, 7, 11, 13 and 17 eluted at retention time of 21.317, 23.100, 26.833, 28.750 and 32.417 minutes respectively.

Calibration curve was made by using Waters Empower software. Relative technique and $1^{st}$ Order fit was used for plotting the curve (FIG. 3).

$R^2$ for Calibration curve of Copaxone fractions was 0.996.

Using this standard curve, two batches each of Copaxone and Glatiramer acetate obtained by the process of the present invention were analyzed (FIG. 4) and the results were as follows:

Results with Calibration Curve of Copaxone Fractions:

| Batch No. | Mp (kDa) | Mw (kDa) | Mn (kDa) |
|---|---|---|---|
| Example 7 | 7.98 | 8.76 | 5.91 |
| Example 8 | 7.73 | 8.87 | 6.1 |
| Cop.# 53119 | 6.98 | 8.46 | 5.98 |
| Cop.# 53289 | 7.87 | 9.55 | 6.55 |

Example 1(B)

Figure 5:
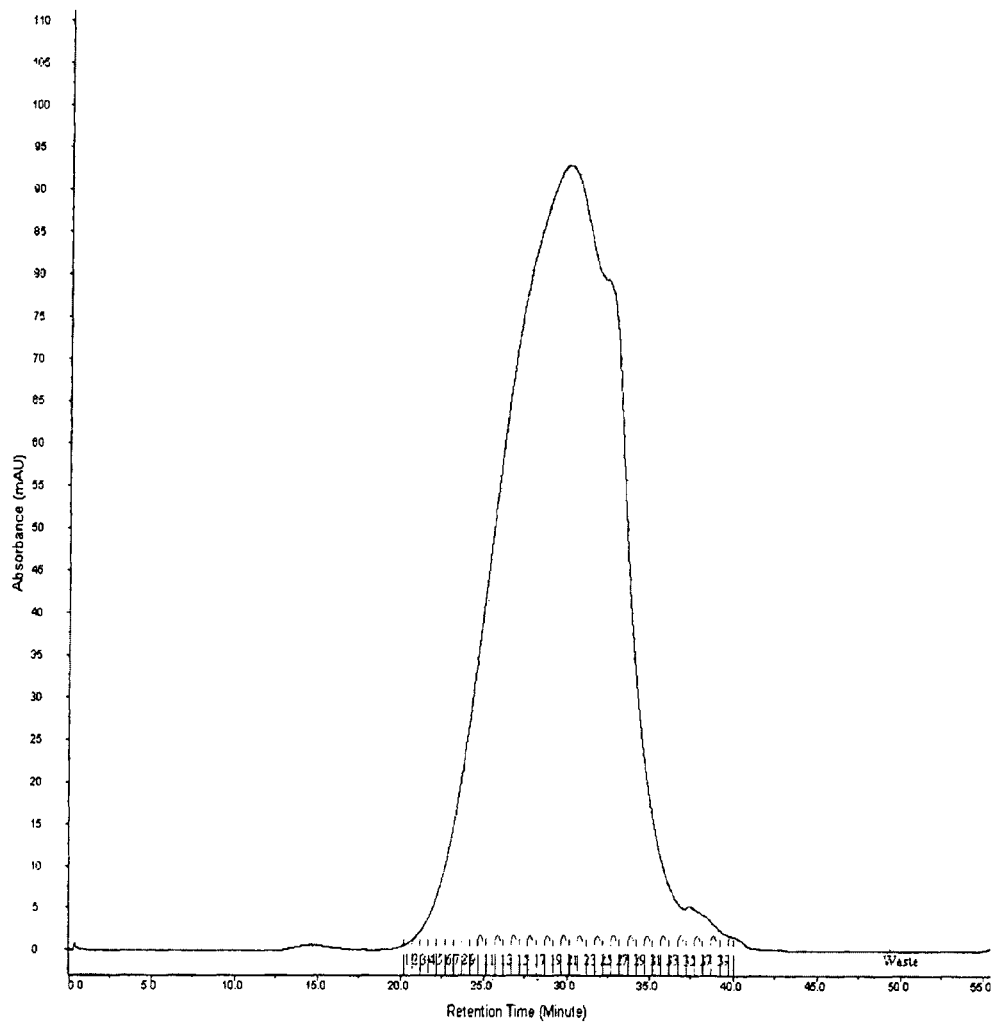
FIG. 5: Graph showing fractionation of Glatiramer acetate prepared by the process of the present invention.

Molecular Weight Determination of Glatiramer Acetate Batches a) Fractionation of Glatiramer Acetate Obtained by the Process of the Present Invention:
  Glatiramer acetate about 40 mg was subjected to GPC on a Superose 12 (10/300 GL), System: Acta purifier using 0.2M Ammonium acetate pH 5.0 as mobile phase, at a flow rate of 0.5 ml/min.
  Glatiramer peak started eluting after about 20 min and ended after about 40 min.
  30 individual fractions were collected within an interval gap of 0.5 minute (FIG. 5) starting from the 21$^{st}$ minute and ending at about 41$^{st}$ min.
  Around 15 fractions were analyzed for polydispersity and molecular weight.
  Fractions were selected in such a way that one of these fractions represents the peak apex molecular weight and other fractions were distributed on either side of the peak apex molecular weight.
  Fractions having polydispersity of less than 1.2 were selected and lyophilized.
  Fractions having polydispersity of more than 1.2 were subjected to further purification so as to obtain fractions having polydispersity less than 1.2.
  Fractions having molecular weight 3 kD, 5 kD, 7 kD, 10 kD and 12 kD were selected to be used as molecular weight markers.
  Molecular weight of these selected fractions were determined using SEC-MALLS [Conditions same as mentioned in Example 1(A)]. Mp and polydispersity of these selected fractions are shown in Table below, Characterized Fractions Used as Molecular Weight Markers

| Fraction | Mp(kD) | Polydispersity PD = Mw/Mn |
|---|---|---|
| Fraction # 16 | 12.56 | 1.05 |
| Fraction # 18 | 10.05 | 1.08 |
| Fraction # 22 | 7.38 | 1.17 |
| Fraction # 24 | 5.06 | 1.11 |
| Fraction # 26 | 3.2 | 1.05 |

Figure 6:
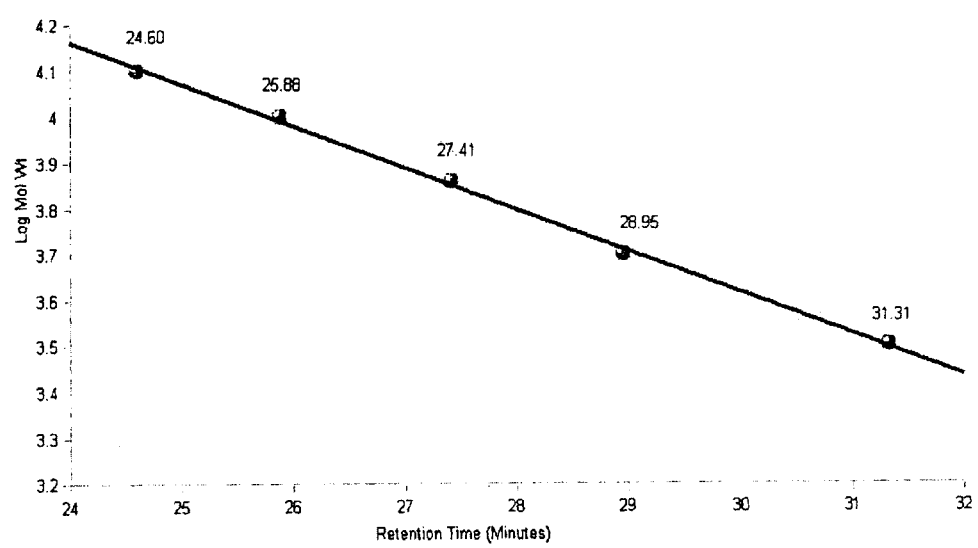
FIG. 6: Calibration curve of fractionated Glatiramer acetate prepared by the process of the present invention.

All these selected fractions were lyophilized and characterized.

b) Use of Characterised Fractions as Molecular Weight Markers for the Determination of Mp, Mw and Mn of Glatiramer by Size Exclusion Chromatography (SEC)/Gel Permeation Chromatography (GPC):
  Fractions 16, 18, 22, 24 and 26 eluted at retention time of 24.60, 25.88, 27.41, 28.95 and 31.31 minutes respectively.
  Calibration curve was made by using Waters Empower software. Relative technique and 1$^{st}$ Order fit was used for plotting the curve (FIG. 6).

$R^2$ for Calibration curve of the characterized fractions was 0.99.

Using this standard curve, two batches each of Copaxone and Glatiramer acetate obtained by the process of the present invention were analyzed (FIG. 7) and the results were as follows:

Results with Calibration Curve of Copaxone Fractions:

| Batch No. | Mp (kD) |
|---|---|
| Glatiramer acetate obtained by process of present invention | 7275 |
| Glatiramer acetate obtained by process of present invention | 7234 |
| P53313 | 7183 |
| P53289 | 7571 |

Example 2

200 g (0.84 moles) of γ-benzyl L-glutamate and 10 g of activated charcoal were suspended in 2.4 L of tetrahydrofuran (THF). 124.6 g (0.42 moles) of triphosgene was added to the obtained mixture and stirred for 0.5 hr at 50-55° C. After the completion of reaction, the reaction mixture was cooled to room temperature, filtered through hyflo bed and nitrogen gas was purged through the obtained filtrate for 2 hr below 35° C. The filtrate was concentrated under vacuum to get an oil. The obtained oil was stripped thrice with 1 L of hexane to get the solid. The obtained solid was stirred with 2 L hexane, filtered, washed with 2 L hexane and dried under vacuum at below 45° C. The dried material was passed through 30 mesh and again re-dried. The re-dried solid was stored at –20° C. in a air-tight container.

Yield: 200 g (100% w/w w.r.t. amino acid), m.p: 92°-94° C.

Example 3

110 g (0.552 moles) of L-tyrosine and activated charcoal (5.5 g) were suspended in 1.32 L of tetrahydrofuran (THF). 89.76 g (0.302 moles) of triphosgene was added to it. The reaction mixture was stirred for 2 hr at 50-55° C. After the completion of reaction, the reaction mixture was cooled to room temperature, filtered through hyflo bed. Nitrogen gas was purged through the obtained filtrate for 2 hr below 35° C. The reaction mixture was then concentrated under vacuum to get a solid mass. The obtained solid mass was stripped thrice with 0.55 L hexane and further stirred with 1.1 L hexane, filtered, washed with 1.1 L hexane and dried under vacuum below 45° C. The dried material was passed through 30 mesh and again re-dried. The re-dried solid was stored at –20° C. in a air-tight container.

Yield: 80 g (73% w/w w.r.t. amino acid). The compound decomposed at 250° C. to 270° C.

Example 4

400 g (1.65 moles) of N$^\epsilon$-trifluoroacetyl L-lysine and activated charcoal (20 g) were suspended in 4.8 L of tetrahydrofuran (THF). 243.3 g (0.82 moles) of triphosgene was added to it. The reaction mixture was stirred for 0.5 hr at 50-55° C. After the completion of reaction, the reaction mixture was cooled to room temperature, filtered through hyflo bed. Nitrogen gas was purged through the obtained filtrate for 2 hr below 35° C. The reaction mixture was then concentrated under vacuum to get an oil. The obtained oil was stripped with 2 L hexane thrice to get a solid. The obtained solid was stirred with 4 L hexane, filtered, washed with 4 L hexane and dried under vacuum below 45° C. The dried material was passed through 30 mesh and again re-dried. The re-dried solid was stored at −20° C. in a air-tight container.

Yield: 415 g (104% w/w w.r.t. amino acid), m.p: 83° C.-86° C.

Example 5

200 g (2.24 moles) of L-alanine was suspended in 4 L of tetrahydrofuran (THF) and the mixture was heated to 50°-55° C. for 1.5 hr. 10 g of activated charcoal and 333 g (1.12 moles) of triphosgene dissolved in 1 L of THF were added to heated suspension over a period of about 10 min at 50-55° C. The reaction mixture was stirred for 1.5 hr at the same temperature and second lot of 333 g (1.12 moles) of triphosgene dissolved in 1 L of THF was added to it over a period of about 10 min followed by stirring the mixture for 1.5 hr at 50-55° C. After the completion of reaction, the mixture was filtered and nitrogen gas was purged through the obtained filtrate for 2 hr below 35° C. The filtrate was concentrated under vacuum below 35° C. to get an oil. 1.6 L of ethyl acetate was added to the obtained oil, stirred for 10 min and filtered through hyflo bed. 13 L of hexane was added to the obtained filtrate to get solid which was filtered, washed with 4 L hexane and dried under vacuum at below 45° C. The dried material was passed through 30 mesh and again re-dried. The re-dried solid was stored at −20° C. in an air-tight container.

Yield: 180 g (90% w/w w.r.t. amino acid), m.p: 91°-92° C.

Example 6

A mixture of L-amino acid NCAs [50 g of N-carboxyanhydride of L-alanine, 35 g of N-carboxyanhydride of γ-benzyl L-glutamate, 83 gm of N-carboxyanhydride of $N^{\epsilon}$-trifluoroacetyl L-lysine, 18 gm of N-carboxyanhydride of L-tyrosine] was dissolved in 3.5 L of anhydrous dioxane and stirred for 30 min. The solution was filtered if any insoluble suspended particle was seen. A solution of 1% diethylamine in anhydrous dioxane (266 ml) was added to the reaction mass in one lot. The resulting mixture was stirred at room temperature for 24 hours at 200-215 rpm. 10 L deionized water was added to the reaction mixture to get white solid. The obtained solid was filtered under vacuum, washed with 10 L deionized water and air dried till LOD NMT 10% was achieved. The obtained solid was passed through 30 mesh sieve.

Yield: 120 g (64.5% w/w)

Example 7

In a reactor was taken 960 ml of ~15% HBr in acetic acid at room temperature and stirred at 200-215 rpm for 30 min until about 25° C. was reached. 115 gm of protected copolymer (from Example 6) was added into the reactor and stirred at about 25° C. at 200-215 rpm for 23 hr. The reaction mixture was quenched in cold water to get a white solid. Ammonia solution was added to it till pH 6-7 was achieved and was stirred at room temperature for about 20 hrs. The solid was filtered, washed with water and air dried. Yield: 75 g (65.2% w/w)

Example 8

75 gm of Trifluoroacetyl copolymer (from example 7) was suspended in 3.75 L of water. 435 ml of Piperidine was added to the suspension in one lot and stirred for 24 hr at room temperature. The reaction mixture was passed through 0.2μ filter, passed through tangential flow filtration having molecular weight cut off (MWCO) cassette of 1 KD, diafiltered with deionized water, then with 0.3% aqueous acetic acid and again with deionized water until pH 5.5-7 was achieved. The obtained solution was then lyophilized to dryness to obtain a white fluffy solid.

Yield: 50.5 g (67.3% w/w), Peak apex molecular weight (Mp)=7980 D.

Alternatively, the obtained solution can be taken as such for formulation.

Example 9

75 gm Trifluoroacetyl copolymer (from example 7) was suspended in 3.75 L of water. 300 ml of diethylamine was added to the suspension in one lot and stirred for 24 hr at room temperature. The reaction mixture was passed through 0.2μ filter, passed through tangential flow filtration having molecular weight cut off (MWCO) cassette of 1 KD, diafiltered with deionized water, then with 0.3% aqueous acetic acid and again with deionized water until pH 5.5-7 was achieved. The obtained solution was then lyophilized to dryness to obtain a white fluffy solid.

Yield: 52.86 g (70.4% w/w), Peak apex molecular weight (Mp)=7730 D.

Alternatively, the obtained solution can be taken as such for formulation.

Example 10

In a reactor was taken 960 ml of ~15% HBr in acetic acid at room temperature and stirred at 200-215 rpm for 30 min until 25° C. was reached. 115 gm of Protected copolymer (Example 6) was added into the reactor and stirred at about 25° C. at 200-215 rpm for 23 hr. The reaction mixture was quenched in cold water to get a white solid. Ammonia solution was added to it till pH 6-7 was achieved and was stirred at room temperature for about 20 hrs. The solid was centrifuged, washed with water and recentrifuged to get a wet solid. The wet solid was suspended in 4.6 L of water. 517 ml of Piperidine was added to the suspension in one lot and stirred for 24 hr at room temperature. The reaction mixture was passed through 0.2μ filter, passed through tangential flow filtration having molecular weight cut off (MWCO) cassette of 1 KD, diafiltered with deionized water, then with 0.3% aqueous acetic acid, and again with deionized water until pH 5.5-7 was achieved. The obtained solution was then lyophilized to dryness to obtain a white fluffy solid.

Yield: 54.5 g (47.39% w/w), Peak apex molecular weight (Mp)=6960 D. Alternatively, the obtained solution can be taken as such for formulation.

Example 11

In a reactor was taken 960 ml of ~15% HBr in acetic acid at room temperature and stirred at 200-215 rpm for 30 min until 25° C. was reached. 115 gm of Protected copolymer (Example 6) was added into the reactor and stirred at about 25° C. at 200-215 rpm for 23 hr. The reaction mixture was quenched in cold water to get a white solid. Ammonia solution was added to it till pH 6-7 was achieved and was stirred at room temperature for about 20 hrs. The solid was centrifuged, washed with water and recentrifuged to get a wet solid. The wet solid was suspended in 4.6 L of water. 287 ml of Diethylamine was added to the suspension in one lot and stirred for 24 hr at room temperature. The reaction mixture was passed through 0.2μ filter, passed through tangential flow filtration having molecular weight cut off (MWCO) cassette of 1 KD, diafiltered with deionized water, then with 0.3% aqueous acetic acid, and again with deionized water until pH 5.5-7 was achieved. The obtained solution was then lyophilized to dryness to obtain a white fluffy solid.

Yield: 55.86 g (48.57% w/w), Peak apex molecular weight (Mp)=7291 D.

Alternatively, the obtained solution can be taken as such for formulation.

Example 12

480 ml of approx. 15% HBr in acetic acid was taken in a reactor at room temperature and stirred at 200-215 rpm for 30 min until about 25° C. was reached. 2.4 gm of resorcinol was added to it and stirred for 2 hr at 25° C. at 200-215 rpm. 60 gm of Protected copolymer (Example 6) was added into the reactor and stirred at about 25° C. at 200-215 rpm for 23 hr. The reaction mixture was quenched in cold water to get a white solid. Ammonia solution was added to it till pH 6-7 was achieved and was stirred at room temperature for about 20 hrs. The solid was filtered, washed with water and air dried. Yield: 36 g (60% w/w).

The same example was repeated using other bromine scavenger such as Tyrosine, sodium bisulfate, sodium thiosulphate, naphthalene, 1-naphthol or 2-naphthol.

Example 13

36 gm of Trifluoroacetyl copolymer (from Example 12) was suspended in 1.8 L of water. 209 ml of Piperidine was added to the suspension in one lot and stirred for 24 hr at room temperature. The reaction mixture was passed through 0.2µ filter, passed through tangential flow filtration having molecular weight cut off (MWCO) cassette of 1 KD, diafiltered with deionized water, then with 0.3% aqueous acetic acid and again with deionized water until pH 5.5-7 was achieved. The obtained solution was then lyophilized to dryness to obtain a white fluffy solid.

Yield: 24.48 g (68% w/w)

Alternatively, the obtained solution can be taken as such for formulation.

Example 14

36 gm of Trifluoroacetyl copolymer (from Example 12) was suspended in 1.8 L of water. 144 ml of Diethylamine was added to the suspension in one lot and stirred for 24 hr at room temperature. The reaction mixture was filtered through 0.2µ, passed through tangential flow filtration having molecular weight cut off (MWCO) cassette of 1 KD, diafiltered with deionized water, then with 0.3% aqueous acetic acid and again with deionized water until pH 5.5-7 was achieved. The obtained solution was then lyophilized to dryness to obtain a white fluffy solid.

Yield: 26.8 g (74.4% w/w)

Alternatively, the obtained solution can be taken as such for formulation.

Example 15

In a reactor was taken 460 ml of ~15% HBr in acetic acid and 460 ml of acetic acid at room temperature and stirred at 200-215 rpm for 30 min until 25° C. was reached. 4.6 gm of phenol was added to it and stirred for 2 hr at about 25° C. at 200-215 rpm. 115 gm of Protected copolymer (Example 6) was added into the reactor and stirred at about 25° C. at 200-215 rpm for 21-23 hr. The reaction mixture was quenched in cold water to get a white solid. Ammonia solution was added to it till pH 6-7 was achieved and was stirred at room temperature for about 20 hrs. The solid was centrifuged, washed with water and recentrifuged for about 3 hr to obtain wet solid. The wet solid was suspended in 4.6 L of water. 287 ml of diethylamine was added to the suspension in one lot and stirred for 24 hr at room temperature. The reaction mixture was passed through 0.2µ filter, passed through tangential flow filtration having molecular weight cut off (MWCO) cassette of 1 KD, diafiltered with deionized water, then with 0.3% aqueous acetic acid, and again with deionized water until pH 5.5-7 was achieved. The obtained concentrated solution was sterile filtered and stored at 2° C. to 8° C. in a sterile PET G bottle, which was covered with black polythene bag.

Yield: 1670 L (36.1 mg/ml), Peak apex molecular weight (Mp)=6974 D.

The obtained concentrated solution having a concentration (assay) of Glatiramer acetate of about 30-40 mg/ml can be taken as such for formulation.

Example 16

In a reactor was taken 460 ml of ~33% HBr in acetic acid and 460 ml of acetic acid at room temperature and stirred at 200-215 rpm for 30 min until about 25° C. was reached. 4.6 gm of phenol was added to it and stirred for 2 hr at 25° C. at 200-215 rpm. 115 gm of Protected copolymer (Example 6) was added into the reactor and stirred at 25° C. at 200-215 rpm for 21 hr. The reaction mixture was quenched in cold water to get a white solid. Ammonia solution was added to it till pH 6-7 was achieved and was stirred at room temperature for about 20 hrs. The solid was centrifuged, washed with water and recentrifuged for about 3 hr. The wet solid was suspended in 4.6 L of water. 287 ml of diethylamine was added to the suspension in one lot and stirred for 24 hr at room temperature. The reaction mixture was passed through 0.2µ filter, passed through tangential flow filtration having molecular weight cut off (MWCO) cassette of 1 KD, diafiltered with deionized water, then with 0.3% aqueous acetic acid, and again with deionized water until pH 5.5-7 was achieved. The obtained concentrated solution was sterile filtered and stored at 2° C. to 8° C. in a sterile PET G bottle, which was covered with black polythene bag.

Yield: 1690 L (35 mg/ml), Peak apex molecular weight (Mp)=7324 D.

The obtained concentrated solution having a concentration (assay) of Glatiramer acetate about 30-40 mg/ml can be taken as such for formulation.

Example 17

Analysis of Amino Acid by UPLC:
Chromatographic Conditions:
Column: AccQ.Tag Ultra Column 2.1×100 mm, 1.7 µm
Mobile Phase A: Eluent A1 (5% AccQ.Tag mobile phase diluted with water)
Mobile Phase B: Eluent B (as such)
Wavelength: 260 nm
Sampling Rate: 10 points/sec
Column Temp: 55° C.
Sample Temp: 20° C.
Flow Rate: 0.7 ml/min
Programming: Gradient program
Derivatization: Derivatization by AccQ. Tag derivatization agent The test results for molar fractions of amino acids are summarized in Table 12:

| Amino Acids | Std. Molar fraction | Std. Molar fraction range | COPAXONE B. No: 538518 | Example 7 | Example 8 |
|---|---|---|---|---|---|
| L-Tyrosine | 0.095 | 0.085-0.104 | 0.099 | 0.090 | 0.100 |
| L-Glutamic Acid | 0.141 | 0.127-0.155 | 0.132 | 0.140 | 0.140 |
| L-Lysine | 0.338 | 0.304-0.372 | 0.347 | 0.350 | 0.330 |
| L-Alanine | 0.427 | 0.384-0.470 | 0.422 | 0.420 | 0.430 |

Example 18

Peptide Mapping Using Trypsin Enzyme 0.25 mg of Glatiramer acetate was digested using 5 μg of Trypsin (treated with tosyl-L-phenyl alanine chloromethyl ketone) in 0.05M Tris buffer pH 7.5 at a temperature of about 37° C. This treatment was continued for about 4 hours to obtain peptide fragments of short chain lengths. These fragments were separated and analyzed using HPLC-UV on C18, 250×4.6 mm HPLC column to obtain a chromatogram. Chromatogram thus obtained was compared with the chromatogram obtained by subjecting Copaxone to the same treatment as mentioned above.

Example 19

Peptide Mapping Using Trypsin and Carboxypeptidase B Enzyme 3.5 mg of Glatiramer acetate was digested using 7 μg of Trypsin (treated with tosyl-L-phenyl alanine chloromethyl ketone) in 0.05M Tris buffer pH 7.5 at a temperature of about 37° C. This treatment was continued for about 4 hours to obtain peptide fragments of short chain length. This mixture of peptide fragments obtained after trypsin treatment was subjected to 20 μg of carboxypeptidase B treatment at 37° C. for about 18 hours which results in further fragmentation of the peptide chain. These fragments were separated and analyzed using HPLC-UV on C18, 250×4.6 mm HPLC column to obtain a chromatogram. Chromatogram thus obtained was compared with the chromatogram obtained by subjecting Copaxone to the same treatment as mentioned above.

Example 20

(A) Composition

| Ingredient | Quantity (mg/1 ml) |
|---|---|
| Glatiramer Acetate | 20.00 |
| Mannitol | 40.00 |
| Water for Injection | q.s. 1.0 ml |

(B) Preparation

Mannitol was dissolved in part quantity of water for injection by stirring. The concentrated solution of Glatiramer acetate API was added to this mannitol solution and mixed. The final volume was made up with the remaining quantity of water for injection. The pH of the solution was checked (pH limit: 5.5 to 7.0). The final solution was filtered using 0.2μ sterilizing grade polyethersulfone filter. The filtered solution was filled into vials and the vials were sealed.

Example 21

Statistical Technique for Evaluating the Consistency and Reproducibility of the Process for Preparation of Molecular Weight Markers Five sets of molecular weight markers were generated using different batches of Glatiramer acetate. Each set contained seven molecular weight markers having different molecular weights in the range of 2000 to 13000 daltons, as shown in Table below,

| Set 1 | Set 2 | Set 3 | Set 4 | Set 5 |
|---|---|---|---|---|
| 12628 | 12208 | 12215 | 12373 | 12580 |
| 9892 | 9241 | 9915 | 10128 | 8939 |
| 7019 | 7991 | 6706 | 7870 | 6556 |
| 6185 | 6335 | 6073 | 6267 | 5890 |
| 5163 | 5704 | 5532 | 5631 | 4969 |
| 4888 | 4612 | 4755 | 4000 | 4069 |
| 2709 | 2989 | 3775 | 3292 | 3671 |

Statistical process of randomization was applied to these five sets of molecular weight markers to generate a larger set of molecular weight markers, each set containing seven molecular weight markers as in Table below,

| 1 | 2 | 3 | 4 | 5 | 6 | 7 | 8 | 9 | 10 |
|---|---|---|---|---|---|---|---|---|---|
| 12215 | 12628 | 12373 | 12628 | 12215 | 12215 | 12215 | 12373 | 12373 | 12628 |
| 8939 | 10128 | 9241 | 8939 | 10128 | 9892 | 9892 | 9915 | 9915 | 9915 |
| 7991 | 6556 | 7991 | 7991 | 6556 | 7991 | 6706 | 6706 | 6706 | 6556 |
| 6267 | 6073 | 6335 | 6073 | 6267 | 6073 | 5890 | 5890 | 6267 | 6185 |
| 4969 | 5163 | 5704 | 5532 | 5704 | 4969 | 5532 | 5704 | 4969 | 4969 |
| 4755 | 4069 | 4069 | 4069 | 4000 | 4755 | 4612 | 4755 | 4755 | 4755 |
| 2989 | 3775 | 2989 | 2709 | 2989 | 2989 | 3671 | 3775 | 3671 | 3292 |

These larger sets of markers were then used to determine the peak apex molecular weight of Glatiramer acetate batch and the results were as shown in table below,

| Batch No. | Min | Max | Diff | Mean | SD | RSD | Confidence interval (95% level) |
|---|---|---|---|---|---|---|---|
| Batch 1 | 6811 | 7108 | 297 | 6916 | 95.00 | 1.37 | 6971 |
| Batch 2 | 6739 | 7036 | 297 | 6842 | 95.61 | 1.40 | 6897 |
| Batch 3 | 6763 | 7060 | 297 | 6867 | 95.37 | 1.39 | 6922 |

This randomization study revealed that any permutation-combination of molecular weight markers taken from different sets will provide predictable results based on 95% confidence interval. This indicates that the process of the present invention for preparation of molecular weight markers was consistent, reproducible and was not affected by batch to batch variation of the starting material. Molecular weight markers generated using the process of present invention from different batches of Glatiramer acetate provided predictable results based on 95% confidence interval.

We claim:

1. A process for preparation of polypeptide fractions with random amino acid sequence similar to that of Glatiramer acetate, which serve as molecular weight markers for Glatiramer acetate, comprising the steps of, a) subjecting a polypeptide mixture with random amino acid sequence, which is similar to Glatiramer acetate in terms of amino acid composition and molar ratio of amino acids, to Gel Permeation Chromatography (GPC)/Size Exclusion Chromatography (SEC) to obtain polypeptide fractions having molecular weights in the range of 2 kD to 30 kD and having random amino acid sequence;

b) selecting polypeptide fractions from said polypeptide fractions obtained in step a) such that one of the fractions represents the peak apex molecular weight and other fractions are distributed on either side of the peak apex molecular weight; and c) calculating tailing factor of the selected polypeptide fractions.

2. The process as claimed in claim 1, wherein said tailing factor of selected polypeptide fractions is in the range of 0.8 to 1.

3. The process as claimed in claim 1, wherein polydispersity of said selected polypeptide fractions is less than or equal to 1.20.

4. The process as claimed in claim 3, wherein said polypeptide mixture is Glatiramer acetate.

5. The process as claimed in claim 4, wherein said Glatiramer acetate is prepared by a process comprising the steps of, a) treating protected copolymer with about 7% to 20% HBr in acetic acid at about 25° C. for about 21-23 hours to obtain trifluoroacetyl copolymer;

b) treating said trifluoroacetyl copolymer with a base selected from diethylamine, dimethylamine or diisopropylamine to obtain completely deprotected copolymer;

c) converting completely deprotected copolymer to Glatiramer acetate.

6. The process as claimed in claim 5, wherein said treatment in step a) is carried out at 25° C.±0.2° C. and said HBr in acetic acid is optionally pre-treated with a scavenger selected from phenol, resorcinol, tyrosine, sodium bisulfite, sodium thiosulphate, naphthalene, 1-naphthol or 2-naphthol.

7. The process as claimed in claim 5, wherein said conversion of completely deprotected copolymer to Glatiramer acetate comprises the steps of, a) concentrating an aqueous solution of completely deprotected copolymer to minimum volume using Tangential Flow Filtration (TFF) by passing through a cassette of polyether sulphone membrane having molecular weight cut off (MWCO) of 1 KD;

b) washing the concentrated solution of step a) with water till pH 8 to 9 is achieved followed by washing with 0.3% acetic acid solution for salt exchange to get Glatiramer acetate; and c) washing Glatiramer acetate obtained in step b) with water till pH 5.5 to 7 is achieved to get pure Glatiramer acetate.

8. The process as claimed in claim 1, wherein said selected polypeptide fractions are used as molecular weight markers for determining the molecular weight of Glatiramer acetate batch by a process comprising the steps of, a) calibrating the SEC/GPC column using said selected polypeptide fractions;

b) establishing a relationship between retention time and log molecular weight of these selected fractions by means of a calibration curve;

c) subjecting Glatiramer acetate batch whose molecular weight is to be determined to SEC/GPC to obtain the retention time;

d) using the relationship between the retention time and log molecular weight to determine the molecular weight of Glatiramer acetate batch.

9. The process as claimed in claim 7, wherein said Glatiramer acetate has an average molecular weight in the range of 5000-9000 Daltons and wherein said Glatiramer acetate is used in the preparation of pharmaceutical composition either as a lyophilized solid or as an aqueous solution containing Glatiramer acetate in the concentration range of about 25-45 mg/ml.

10. The process as claimed in claim 5, wherein Glatiramer acetate is further characterized by peptide mapping using trypsin and carboxypeptidase B, comprising the steps of, a) enzymatic treatment of Glatiramer acetate using trypsin to obtain peptide fragments of short chain lengths;

b) treating the peptide fragments obtained in step a) with carboxypeptidase B resulting in further fragmentation of peptide chain;

c) separating and analyzing peptide fragments obtained in step b) using HPLC technique to obtain the chromatogram; and d) comparing the chromatogram thus obtained with the chromatogram of reference standard to determine the structural similarity.

11. The process as claimed in claim 10, wherein said reference standard is known Glatiramer acetate.

12. The process as claimed in claim 1, wherein said GPC/SEC is carried out on Superose-12 or Superdex-75 column using mobile phase selected from ammonium acetate or ammonium formate in a concentration range of 0.1 to 0.3M.

13. The process as claimed in claim 12, wherein column is Superose-12 (10×300 GL); column loading is not more than 50 mg and flow rate is adjusted in the range of 0.4 to 0.6 ml/min.

14. The process as claimed in claim 1, wherein said polypeptide fractions obtained in step a) are lyophilized and wherein the Mp (peak apex molecular weight) of said fractions is determined using SEC-MALLS (Size Exclusion Chromatography Multi-Angle Laser Light Scattering).

15. The process as claimed in claim 7, wherein the molecular weight of said Glatiramer acetate is determined by the process claimed in claim 8 and wherein said Glatiramer acetate has brominated tyrosine content not more than about 0.15%, when tested by reverse phase HPLC and diethylamide content not more than about 5000 ppm, when tested by ion chromatography method.

16. The process as claimed in claim 15, wherein peak apex molecular weight of Glatiramer acetate batch is determined and wherein said SEC/GPC column is selected from Superose-12 or Superdex-75 and mobile phase is selected from 0.1 to 0.3 M ammonium actetate or ammonium formate.

17. The process as claimed in claim 1, wherein the consistency and reproducibility of said process is tested by a method comprising the steps of, a) obtaining multiple set of molecular weight markers, by the process of claim 1, from different batches of Glatiramer acetate, each set containing molecular weight markers having molecular weight in the range of 2000 to 13000 daltons;

b) assigning molecular weight markers from each set obtained in step a) using statistical process of randomization to further generate a larger set of molecular weight markers; and c) using these larger sets obtained in step b) as molecular weight markers to determine the molecular weight of a latiramer acetate batch by GPC.

18. The process as claimed in claim 17, wherein said molecular weight markers provide predictable results based on 95% confidence interval proving consistency and reproducibility of the process for preparation of molecular weight markers.

* * * * *

UNITED STATES PATENT AND TRADEMARK OFFICE
CERTIFICATE OF CORRECTION

PATENT NO. : 9,029,507 B2  
APPLICATION NO. : 13/985416  
DATED : May 12, 2015  
INVENTOR(S) : Sathe et al.

Page 1 of 1

It is certified that error appears in the above-identified patent and that said Letters Patent is hereby corrected as shown below:

On the Title Page

In Column 1, under "Prior Publication Data", Line 2, after "Dec. 5, 2013", insert
--¶(30) Foreign Application Priority Data
Feb. 14, 2011 (IN) 409-MUM-2011--, therefor In the Claims In Column 32, Line 48, in Claim 16, delete "15," and insert --8,--, therefor In Column 32, Line 52, in Claim 16, delete "actetate" and insert --acetate--, therefor In Column 32, Line 67, in Claim 17, delete "latiramer" and insert --Glatiramer--, therefor Signed and Sealed this
Eighth Day of December, 2020

Andrei Iancu
*Director of the United States Patent and Trademark Office*